US006380156B1

(12) United States Patent
Rinehart et al.

(10) Patent No.: US 6,380,156 B1
(45) Date of Patent: Apr. 30, 2002

(54) TOTAL SYNTHESIS OF THE AMINO HIP ANALOGUE OF DIDEMNIN A

(75) Inventors: Kenneth L. Rinehart, Urbana; Alexandra J. Katauskas, Lincoln, both of IL (US)

(73) Assignee: The Board of Trustees of the University of Illnois, Urbana, IL (US)

( * ) Notice: Subject to any disclaimer, the term of this patent is extended or adjusted under 35 U.S.C. 154(b) by 0 days.

(21) Appl. No.: 09/284,905

(22) PCT Filed: Oct. 24, 1997

(86) PCT No.: PCT/US97/19211

§ 371 Date: Jun. 28, 1999

§ 102(e) Date: Jun. 28, 1999

(87) PCT Pub. No.: WO98/17302

PCT Pub. Date: Apr. 30, 1998

Related U.S. Application Data
(60) Provisional application No. 60/029,109, filed on Oct. 24, 1996.

(51) Int. Cl.$^7$ .............................. C07K 5/12; A61K 37/00
(52) U.S. Cl. ................. 514/11; 514/9; 514/10; 530/317; 530/323; 530/329; 530/330; 530/331; 530/333; 530/335; 530/338; 530/339; 560/1
(58) Field of Search .................. 530/317, 323, 530/329–331, 333, 335, 338, 339; 514/9–11; 560/1

(56) References Cited

PUBLICATIONS

Hamada et al., "Efficient Total Synthesis of Didemnins A and B", *J. Am. Chem. Soc.*, 1989, vol. 111, pp. 669–673.
Harris et al., "Synthetic Studies of Didemnins, III. Synthesis of Statine and Isostatine Stereoisomers", *Tetrahedron* vol. 44, No. 12, pp. 3489–3500 (1988).
Jouin et al., "An Improved Synthesis of β–Keto Ester Units In Didemnins, Using 2,2o–Carbonyl–Bis(3, 5–Dioxo–3–Methyl–1,2,4–Oxadiazolidine)", *Tetrahedron Letters*, vol. 29, No. 2, pp. 2661–2664 (1988).
Rinehart et al., "Synthesis and Properties of the Eight Isostatine Stereoisomers", *J. Org. Chem.*, vol. 57, pp. 3007–3013 (1992).

*Primary Examiner*—Bennett Celsa
(74) *Attorney, Agent, or Firm*—Ernest V. Linek; Banner & Witcoff, Ltd.

(57) ABSTRACT

Disclosed is a synthetic method for the preparation of analogs of Didemnin A (1), particularly the Amino-Hip analog of Didemnin A, also known as "AipDidemnin A" (8). These compounds have the following structures:

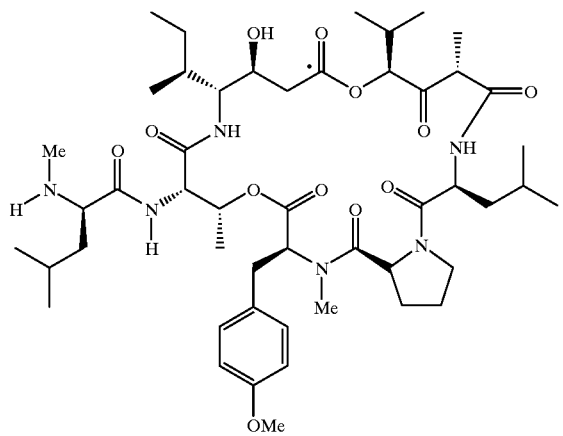

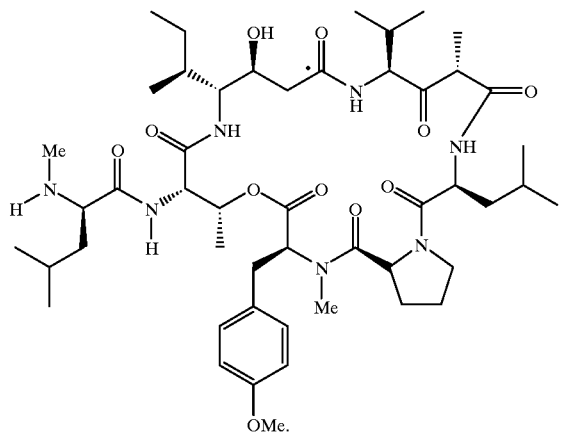

8 Claims, 8 Drawing Sheets

TOTAL SYNTHESIS OF THE AMINO HIP ANALOGUE OF DIDEMNIN A

This application is a 371 of PCT/US97/19211 filed Oct. 24, 1997 which claims benefit of Prov. No. 60/029,109 filed Oct. 24, 1996.

BACKGROUND OF THE INVENTION

Didemins were isolated from the Caribbean tunicate *Trididemnum solidum*[1]. These cyclic depsipeptides possess a variety of biological activities including in vitro and in vivo antiviral, antitumor, and immunosuppressive activities.[2-5] They are potent inhibitors of L1210 leukemia cells in vitro, and are also active in vivo against P388 leukemia and B16 melanoma.[3] Didemnin B, a more active compound of this class, is approximately twenty times more cytotoxic than didemnin A in vitro and has undergone phase II clinical trials for antitumor activity.[3] Both didemnins A and B exhibit antiviral activity against DNA and RNA viruses, with didemnin B being more active.[4] The structures of didemnins A and B have been established as 1 and 2, respectively.[6]

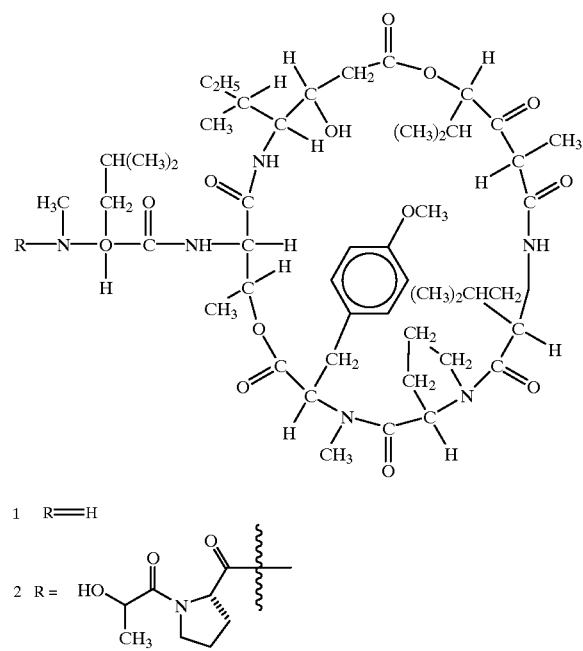

Structure activity relationship studies have been somewhat limited due to the restricted number of available modifications of the extracted natural compounds. Although the bioactivity of didemnin B has been attributed to its side chain,[1b] few other structural features have been examined. An X-ray crystal structure of didemnin B by Hossain, et al.,[7] shows that the β-turn side chain, the isostatine hydroxyl group, and the tyrosine residue extend outward from the rest of the molecule, leading to speculation about their importance for liological activity. Structural changes in those areas have shown these features to be essential for activity.[8]

Although many studies have shed light on the pharmacology and chemistry of didemnins, little is known about their mechanism of action. However, recent biochemical studies of possible binding sites have provided promising results. Studies performed by Shen, et al.,[9] have shown that didemnin B binds to a site on Nb2 node lymphoma cells and that this binding may b responsible for the immunosuppressive activity. Schreiber and co-workers[10] have reported that didemnin A binds elongation factor 1α (EF-1α) in a GTP-dependent manner which suggests EF-1α may be the target responsible for the ability of didemnins to inhibit protein synthesis.

SUMMARY OF THE INVENTION

We present here synthetic studies toward a modified macrocycle which possesses an amide bond in place of an ester bond (3). A modification such as, this is likely to result in an increase in hydrogen bonding at the active site, and thus, provide more active compound. In addition, the facile nature of the C—O bond leads us to believe replacement of these C—O bonds with C—N bonds may improve the stability of these compounds.

Synthetic Strategy.

The retrosynthetic disconnections which formed the basis of our plan for the preparation amino-Hip analogue 3 of didemnin A are illustrated in Scheme I. We envisaged disconnection of the amide function between N,O—Me$_2$-L-tyrosine and L-proline to give the linear heptapeptide 4 and disconnection between L-threonine and isostatine (3S, 4R, 5S) to afford the two units: a tripeptide unit 5 comprised of N—Me-leucine, threonine, and N,O—Me$_2$-tyrosine; and a tetrapeptide unit 6 comprised of isostatine, α-α' aminoisovaleryl) propionyl (Aip), leucine, and proline.

Scheme I

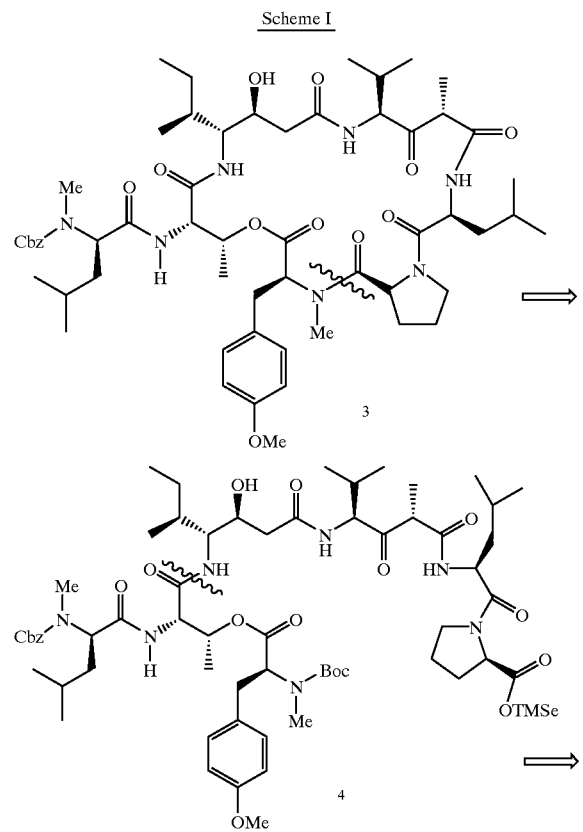

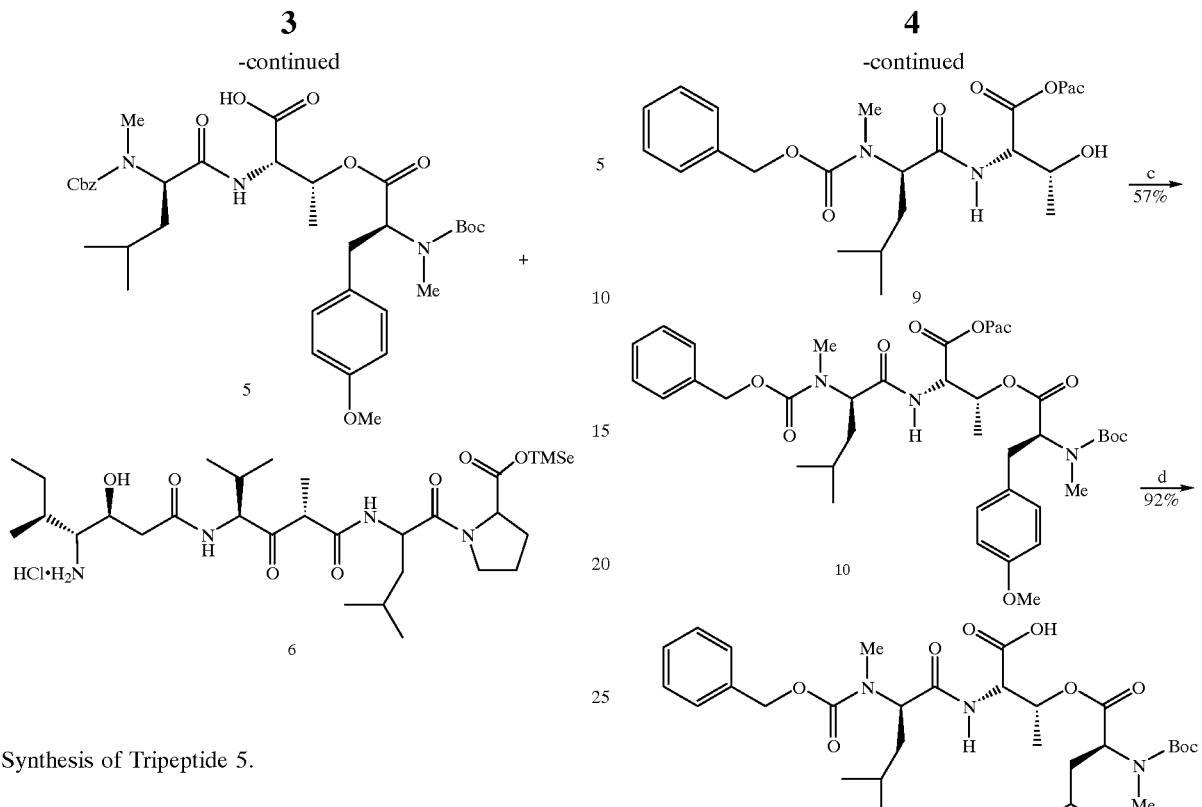

Reagents: a) (i) CH₃I, NaH, THF; (ii) L-ThrOEt, DCC. CH₂Cl₂; b) (i) KOH, MeOH; (ii) phenacylBr, Et₃N, EtOAc; c) BocMe₂TryOH, DCC, DMAP, CH₂Cl₂; d) Zn, HOAc/H₂O.

Synthesis of Tetrapeptide 6.

The construction of fragment 6 involves two novel sub-units (2S,4S)-aminoisovalerylpropionic acid (Aip) and (3S, 4R, 5S)-isostatine (Ist). The synthesis of the required isostatine derivative involves (2R, 3S)-allo-isoleucine. The expensive conversion to the hydroxy acid with retention and its conversion in two steps to the amino acid with inversion (Scheme III).[18] Conversion of (2S, 3S)-isoleucine to the corresponding α-hydroxy acid 12 was accomplished by using a well-known procedure[19] that allows overall retention of configuration via a double inversion. Esterification was carried out with acetyl chloride in methanol, and the corresponding α-hydroxy methyl ester was transformed into the tosloxy methyl ester 13. Treatment of the tosylate with sodium azide in DMF provided the α-azido ester 14 stereo-selectively. Saponification of the ester afforded the α-azido acid 15. Hydrogenation of the azide to the free amine proceeded readily in methanol as atmospheric pressure using Pearlman's catalyst (20% palladium hydroxide on carbon),[20] to afford (2S, 3S)-allo-isoleucine 16.

Synthesis of Tripeptide 5.

Preparation of the diprotected tripeptide unit is shown in Scheme II. Our approach began with methylation of the uncommon amino acid, Cbz-D-leucine, 7, with CH₃I/NaH[11]. Coupling of the derivative Cbz-D-MeLeuOH with the hydroxyl group of the threonine derivative L-TheOEt[12] was accomplished with dicyclohexylcarbodiimide (DCC)[13] to provide the dipeptide E8. Ester hydrolysis with potassium hydroxide afforded the desired carboxylic acid which was then protected as a phenacyl (Pac) ester 9. Coupling with the tyrosine derivative BocMe₂TryOH[14] followed by removal of the Boc protecting group[15] afforded 10. Removal of the phenacyl function[17] provided the key fragment 5.

Scheme II

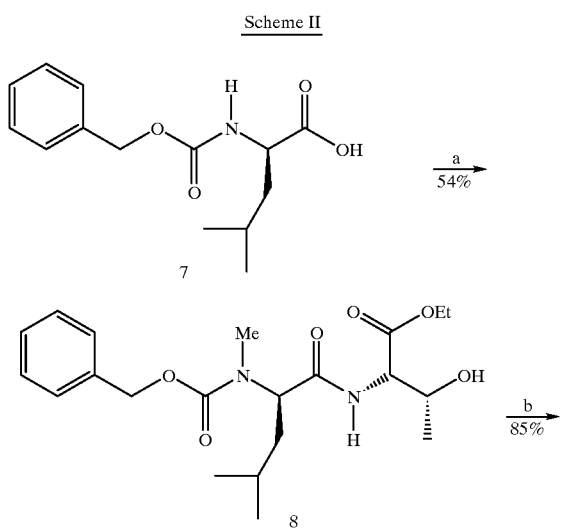

Scheme II

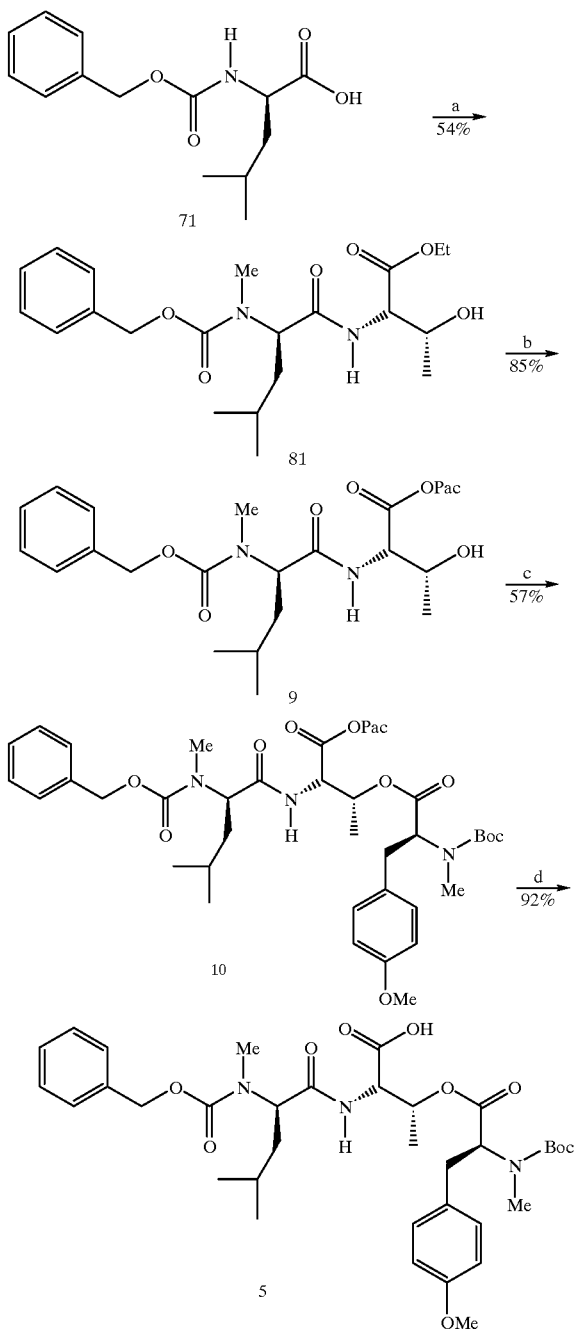

Reagents: a) (i) CH₃I, NaH, THF; (ii) L-ThrOEt, DCC, CH₂Cl₂;
b) (i) KOH, MeOH; (ii) phenacylBr, Et₃N, EtOAc;
c) BocMe₂TyrOH, DCC, DMAP, CH₂Cl₂;
d) Za, HOAc/H₂O.

The major portion of the isostatine subunit, D-allo-isoleucine, 16, was transformed into the tert-butoxycarbonyl (Boc) acid under standard conditions.[16] After activation of its carboxyl group as the imidazolide by use of carbonyldiimidazole, treatment with the magnesium enolate of ethyl hydrogen malonate afforded the required β-keto ester 18. The reduction by NaBH₄ of the carbonyl group of the β-keto ester was effectively stereospecific, generating the desired (3S, 4R, 5S)-19a as the major product (>10:1) after chromatographic separation. As shown in Scheme IV, saponification afforded the required Boc-(3S, 4R, 5S)-Ist-OH, 20.

Scheme IV

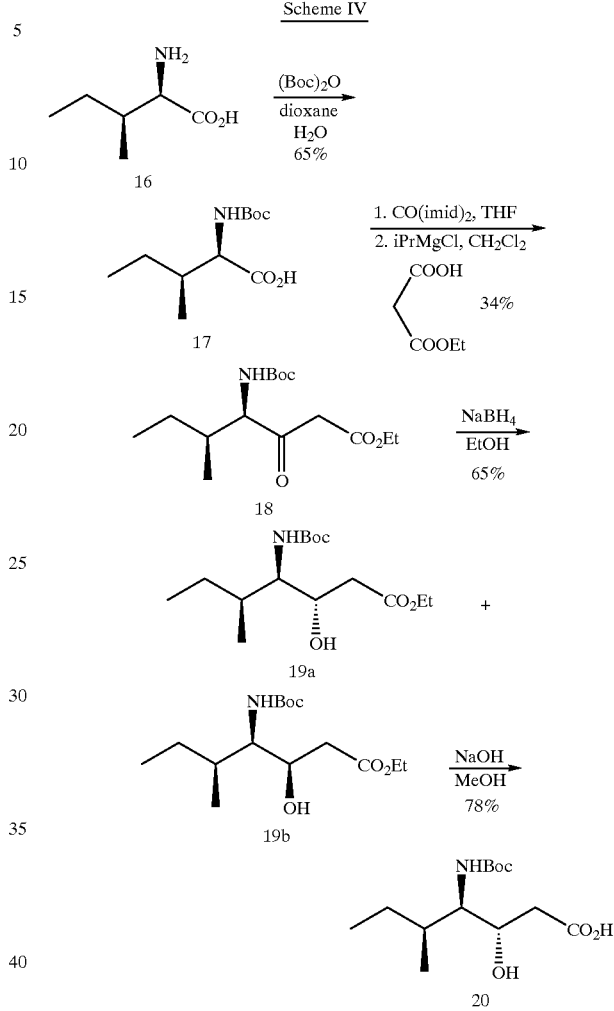

The next step toward the synthesis of the tripeptide fragment (6) involved formation of the amino Hip subunit. This unit was synthesized from Cbz-L-valine, 21, utilizing a procedure based in part on the work of Nagarajan.[21] After activation of its carboxyl group as the imidazolide by use of carbonyl-diimidazole, treatment with the magnesium enolate of ethyl hydrogen methyl malonate (EHMM) afforded the required β-keto ester 22. Sodium borohydride reduction of the β-keto ester produced a diastereomeric mixture of alcohols which were separable by column chromatography. Following saponification and coupling with L-leucine methyl ester (L-LeuOMe), flash chromatography afforded the desired (Pac) bromide provided the protected derivative 24. Oxidation of the secondary alcohol with pyridinium chlorochromate on alumina[22] provided the β-keto amide. Removal of the phenacyl protecting group provided the free acid which was coupled with L-proline trimethylsilylester. Catalytic hydrogenation removed the Cbz protecting group and coupling of the isostating subunit 20 with the amine produced the diprotected tetrapeptide. As shown in Scheme V, the Boc protecting group was then removed under standard conditions[15] to afford the key tetrapeptide unit 6.

Scheme V

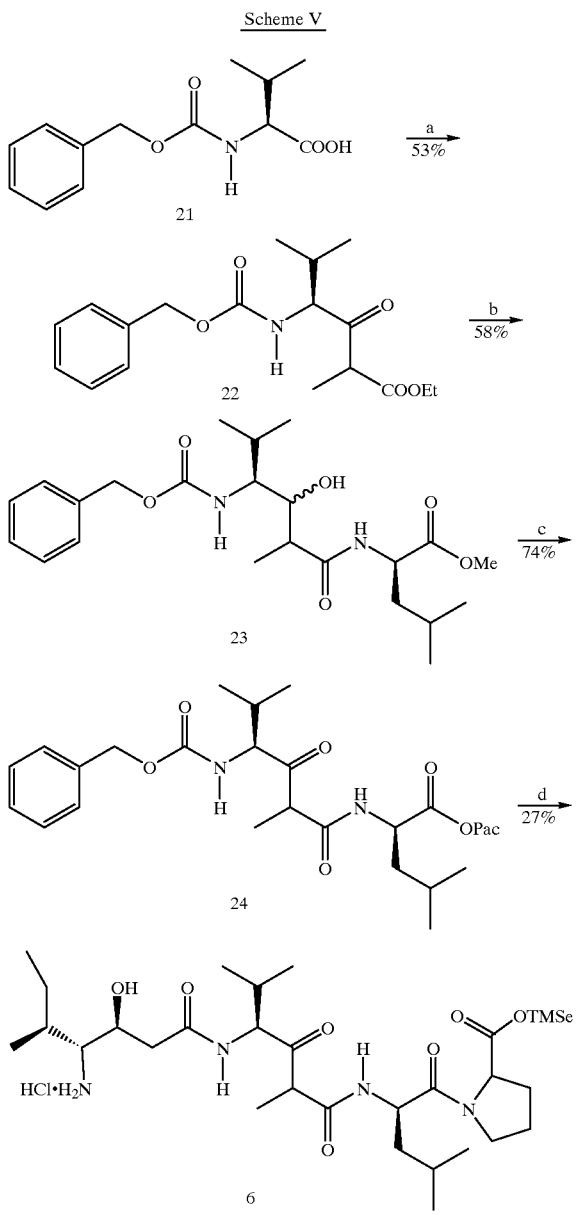

Scheme VI

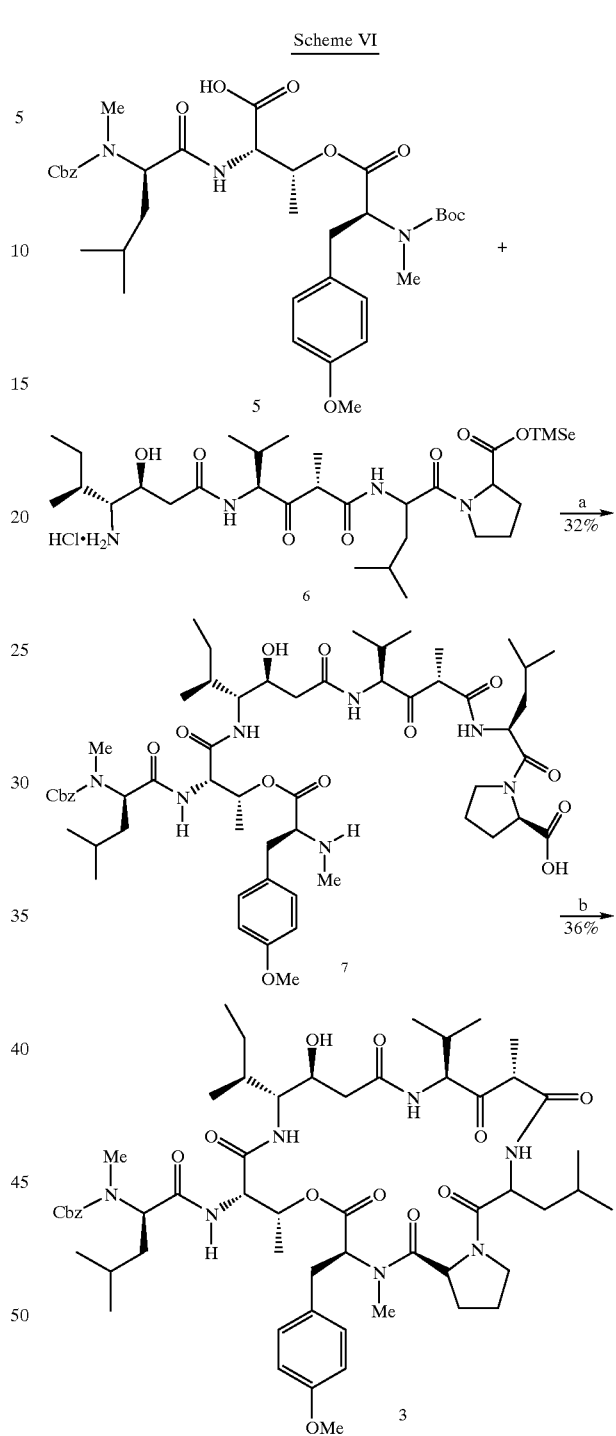

Reagents: a)(i) CO(imid)$_2$, THF; (ii) EHMM, iPrMgBr; b) (i) NaBH$_4$, EtOH; (ii) KOH, MeOH; (iii) LeuOMe, DCC, CH$_2$Cl$_2$; c) (i) KOH, MeOH; (ii) phenacylBr, Et$_3$N, EtOAc; (iii) PCC, Al$_2$O$_3$, CH$_2$Cl$_2$; d) (i) Zn/HOAc; (ii) ProOTMSe, DCC, CH$_2$Cl$_2$; (iii) H$_2$, Pd/C, MeOH; (iv) BocIstOH 16, DCC, CH$_2$Cl$_2$; (v) HCl, dioxane.

Synthesis of Linear Heptapeptide 4.

The synthesis of the linear heptapeptide 4 involved coupling of the two subunits, Cbz-D-MeLeuThe(OMe$_2$TyrBoc)OH, 5, and H-IstAipLeuProOTMSe, 6. A variety of coupling methods (BopCl,[24] DCC,EEDQ[25]) were attempted, however, the EDCI method[26] was shown to be the most efficient for the formation of the triprotected compound 4. Deprotections of the trimethylsilyl ester and the Boc functions were performed under standard conditions to give the monoprotected linear heptapeptide 7. As shown in Scheme VI, cyclization of 7 was achieved by treatment with EDCI to yield the protected compound 3, and catalytic hydrogenation provided the unprotected amino Hip (Aip) analog of didemnin A, 8.

Reagents: a) (i)EDC, NMM, DMF; (ii) TBAF, THF; (iii) TFA, THF; b) EDCl in THF

DETAILED DESCRIPTION OF THE PREFERRED EMBODIMENTS

Figure 1:
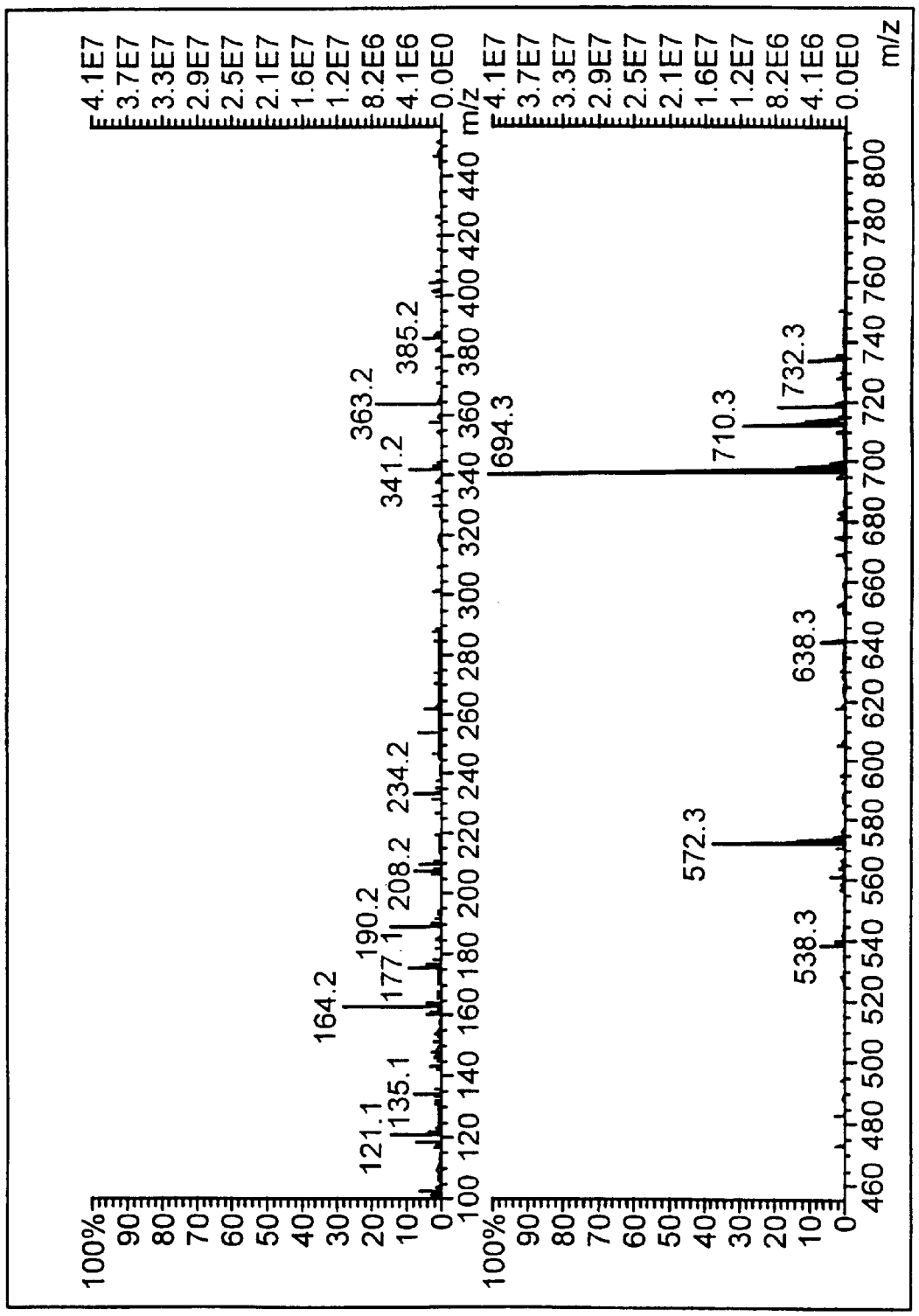
FIG. 1 is a LRFAB mass spectrum of deprotected tripeptide (5).

We have described the total syntheses of the amino Hip analogue of didemnin A. Previous studies have shown that didemnins are subject to hydrolysis and undergo decomposition due to the instability of the ester bonds. Replacement of the ester bond with an amide linkage should increase the maintenance of the active cyclic conformation and, thus, provide a compound of greater activity.

General Experimental Procedures.

$^1$H NMR spectra were recorded on Varian XL-200, General Electric QE-300, Varian XL-400, and General Electric QN-500 spectrometers. $^1$H chemical shifts are references in $CDCl_3$ and methanol-$d_4$ to residual $CHCl_3$ (7.26 ppm) and $CD_2HOD$ (3.34 ppm). Electron impact (EI) mass spectra were recorded on a Finnigan MAT CH-5 DF spectrometer. High resolution (HRFAB) and fast atom bombardment (FAB) mass spectra were recorded on a VG ZAB-SE mass spectrometer operating in the FAB mode sing magic bullet matrix.[27] Microanalytical results were obtained from the School of Chemical Sciences Microanalytical Laboratory. Infrared (IR) spectra were obtained on an IR/32 FTIR spectrophotometer. Solid samples were analyzed as chloroform solutions in sodium chloride cells. Liquids or oils were analyzed as neat films between sodium chloride plates.

Optical rotations (in degrees) were measures with a DIP 360 or a DIP 370 digital polarimeter with an Na lamp (589 nm) using a 5×0.33-cm (1.0 mL) cell. Melting points were determined on a capillary melting point apparatus and are not corrected. Normal phase column chromatography was performed using Merck-kieselgel silica gel (70–230 mesh). Fuji-Davison C18 gel (100–200 mesh was used for reversed phase column chromatography. All solvents were spectral grade. Analytical thin layer chromatography was performed on precoated plates (Merck, F-254 indicator). These plates were developed by various methods including exposure to ninhydrin, iodine, and UV light (254 nm). HPLC was performed with a Waters 900 instrument and an Econosil $C_{18}$ column (Alltech/Applied Science) and a Phenomenex $C_{18}$ column.

THF was distilled from sodium benzophenone ketyl and $CH_2Cl_2$ from $P_2O_5$. Dimethylformamide (DMF), triethylamine ($Et_3N$), and N-methylmorpholine (NMM) were distilled from calcium hydride and stored over KOH pellets. Pyridine was distilled from KOH and stored over molecular sieves. Other solvents used in reactions were reagent grade without purification. Di-tert-butyl dicarbonate [$(BocO)_2O$], dicyclohexycarboniimide (DCC), I-(3-dimethylaminopropyl)-3-ethylcarboniimide hydrochloride (EDCI), dimethylaminophtidine (DMAP). I-hydrozybenzotriazole (HOBT), D- and L-isoleucine, L-tyrosine, L-isoleucine, L-threonin, D-valine, and L-proline were obtained from the Aldrich Chemical Company. All reactions requiring anhydrous conditions were performed under an atmosphere of nitrogen.

N-Benzyloxycarbonyl-N-methyl=D-leucine (Cbz-D-MeLeuOH).

Sodium hydride (60% dispersion, 6.47 g, 162.9 mmol) was added portionwise, with cooling, to a solution of Cbz-D-LeuOH (14.4 g, 54.3 mmol) in THF (21.4 mL) was added portionwise, with cooling. Methyl iodide (27.0 mL, 435 mmol) was then added via a dropping funnel. The reaction was allowed to stand at room temperature for 24 hours. Ethyl acetate (70 mL) was slowly added to the reaction mixture, followed by water, to destroy the excess sodium hydride. The solution was then evaporated to dryness and theoily residue partitioned between ether (30 mL) and water (60 mL). The ether layer was washed the aqueous sodium bicarbonate (5 mL) and the combined aqueous layers were acidified with 4N HCl to pH 3. The solution was extracted with ethyl acetate (3×15 mL) and the extract was washed with 5% aqueous sodium thiosulfate (2×10 mL) and water (10 mL). The solution was dried over sodium sulfate and the solvent evaporated to give an oily residue which crystallized overnight. Recrystallization from petroleum ether produced a white solid (12.7 g, 84%); $[\alpha]^{29}$Na+24.7° (c 0.02, $CHCl_3$), Lit.[11b] $[\alpha]^{29}$D+26.9° (c 0.02, $CHCl_3$); m.p. 71–72° C. (Lit.[11b] 72–73° C.); $^1$H NMR (300 MHz, $CDCl_3$ δ 7.40–7.27 (5H,m), 5.17 (2H,s), 4.74 (1H,m), 2.87 (3H,s), 1.78–1.76 (2H,m), 1.62–1.57 (1H,m), 0.92–0.80 (6H,m); FABMS 280.2 (M+H), 236.2 (M–$CO_2$); HRFABMS Cacd for $C_{15}H_{22}NO_4$ (M+H) 280.1549, Found 280.1556; Anal. Calcd for $C_{15}H_{21}NO_4$; C, 64.48; H, 7.58; N,5.02. Found: C,64.30; H, 7.65; N, 4.93.

L-Threonine Ethyl Ester (L-ThrOEt).

A current of dry HCl was passed through a suspension of L-threonine (35.0 g, 0.29 mol) in absolute ethanol (350 ml), with shaking, until a clear solution formed. The solution then refluxed for 30 minutes, and was evaporated to dryness under reduced pressure, and the oily residue was taken up in absolute ethanol (175 mL) and, again, taken to dryness under reduced pressure. The oily residue was then treated with a saturated solution of ammonia in chloroform. The ammonium chloride was filtered off and the filtrate was taken to dryness at 0° C. under reduced pressure. A yellow solid was isolated (36.2 g. 85%); $[\alpha]^{29}$Na+0.82° (c 5.0, EtOH). Lit.[12] $[\alpha]^{29}$D+0.95° (C 5.0 EtOH); m.p. 51–53° C. (Lit[12] 52–54° C.); $^1$H NMR (200 MHz, $CDCl_3$ w/TMS) δ 4.82 (1H.m), 4.40 (1H,d), 4.05 (2H,q), 1.62 (3H,d), 1.21 (3H;t); FABMS 148.2 (M+H); HRFABMS Calcd for $C_6H_{14}NO_3$ (M+H) 148–0974, found 148.0972.

Z-D-Methylleucylthreonine Ethyl Ester (8).

Z-D-MeLeuOH (2.12 g. 7.59 mmol) was dissolved in 100 mL of $CH_2Cl_2$ and cooled to 0° C. DCC (1.72 g, 8.35 mmol) was added and the solution was stirred at 0° C. for 10 minutes. L-ThrOEt (1.12 g. 7.59 mmol) in a mL of $CH_2Cl_2$ was added and the solution was allowed to warm to rt. After approximately 15 hours, dicyclohexylurea was removed by filtration and washed with $CH_2Cl_2$. The filtrate was washed with 10% citric acid, 5% sodium bicarbonate, and water and dried over sodium sulfate. The solution was evaporated to dryness and the product purified by silica gel column chromatography (hexane/EtOAc=65/35) to afford the product as a yellow oil (2.35 g. 76%); $^1$H NMR (400 MHz, $CDCl_3$) δ 7.36–7.42 (5H,m), 6.73 (1H.d), 6.50 (1H, br s), 5.18 (2H, s), 4.83 (1H,m), 4.51 (1H,m), 4.30 (1H,m), 4.17 (2H,q), 2.81 (3H,s), 1.74 (2H,m), 1.70 (3H,d), 1.68 (2H,m), 1.20 (3H,t), 0.82–0.90 (6H,m); FABMS 431.4 (M+Na), 409.2 (M+H); HBFABMS calcd for $C_{21}H_{33}N_2O_6$ (M+H) 409.2344. Found 409.2339; Anal. Calcd for $C_{21}H_{32}N_2O_6$: C,61.73; H, 7.90; N,6.86. Found=: C, 62.00; H, 8.08; N,7.07.

Z-D Methylleucylthreonine (Z-D-MeLeuThrOH)

Z-D-MeLeuThrOEt (1.80 g, 4.42 mmol) was dissolved in methanol and 2N KOH was slowly added to the mixture at 0° C. The solution was stirred for 2 hours. TLC analysis (CHCl$_3$/MeOH 95:5) showed the reaction to be complete. The mixture was neutralized using 2N CHI. The solvent was then evaporated. The solution was partitioned between ethyl acetate and water and the organic layer separated. Aqueous HCl was added to the aqueous layer to pH 3. This was extracted with ethyl acetate and all o the ethyl acetate extracts were combined. The solution was dried over MgSO$_4$ and the solvent evaporated to give a dark orange oil (1.77 g. 98%) which was used for the next reaction without purification; $^1$H NMR (200 MHz, CDCl$_3$) α 7.36–7.41 (5H,m), 6.72 (1H,s), 6.52 (1H, br s), 5.18 (2H,s), 4.83 (1H,m), 4.51 (1H.,m), 4.30 (1H,m) 2.81 (3H,s), 1.74 (2H, m), 1.70 (3H,d), 1.68 (1H,m), 0.82–0.90 (6H,m); FABMS 381.2 (M+H); HRFABMS Calcd for C$_{19}$H$_{29}$N$_2$O$_6$ (M+H) 381.2026, Found 381.2021; Anal. Calcd for C$_{19}$H$_{28}$N$_2$O$_6$: C, 59.97; H, 7.42; N, 7.37, Found. C, 60.53; H, 7.06; N, 7.11.

Z-D-Methylleucylthreonine Phenacyl Ester (9).

Z-D-MeLeuThrOH (1.50 g. 3.95 mmol) was dissolved in ethyl acetate (25 mL). Triethylamine (0.39 g. 3.95 mmol) and phenacyl bromide (0.079 g., 3.98 mmol) were added and, within a few minutes, a precipitate formed. The mixture was stirred overnight. At this time, water and ether were added and the two layers separated. The organic layer was washed with 0.1N HCl, saturated sodium bicarbonate, and brine, and then dried over MgSO$_4$. The residue was chromatographed on silica gel (hexane/EtOAc=4/1) to give a clear oil (1.71 g, 87%); $^1$H NMR (200 MHz, CDCl$_3$) δ 7.34–7.41 (10H,m), 6.71 (1H,s), 6.52 (1H,br s), 5.27 (2H,s), 5.18 (2H,s), 4.83 (1H,m), 4.61 (1H,m), 4.50 (1H,m)., 2.81 (3H,s), 1.74 (2H.m), 1.70 (3H,d), 1.68 (1H,m), 0.82–0.90 (6H,m); FABMS 537.1 (M+K), 499.1 (M+H); HRFABMS Calcd for C$_{27}$H$_{35}$N$_2$O$_7$ (M+H) 499.2444. Found 499.2450.

N-tert-Butoxycarbonyl-tyrosine (BocTyrOH).[16]

Tyrosine ethyl ester (5.06 g, 25 mmol) was dissolved in 25 mL of water and solid sodium hydroxide was added until litmus paper indicated a neutral pH. Diozane (50 mL) and (Boc)$_2$O (6.12 g, 27.5 mmol) were added with cooling. The reaction was allowed to stir for 2 hours. Water and ether were added and the two layers separated. The organic layer was extracted three times with aqueous sodium hydroxide (IN). The aqueous layers were allowed to sit overnight then neutralized with aqueous HCl and extracted with ether, which was washed with brine and dried over MgSO$_4$. A yellow oil was obtained (6.02 g, 86%); $^1$H NMR (200 MHz, CDCl$_3$) δ 7.10 (2H,d), 6.84 (2H,d), 4.92–5.00 (1H,m), 4.47–4.52 (1H,m), 3.00–3.12 (2H,m), 1.43 (9H,s); EIMS 282.0.

N-tert-Butoxycarbonyl-N,O-dimethyltyrosine (BocMe$_2$TryOH).

A solution of BocTyrOH (5.30 g, 18.8 mmol) and methyl iodide (2.57 mL, 41.4 mmol) in 80 mL of dry THF was cooled at 0° C. and sodium hydride (60% dispersion, 2.47 g, 62.0 mmol) was added. The reaction was allowed to stir at 0° C. for 1 hour, then at rt overnight. Excess sodium hydride was quenched by the dropwise addition of 10 mL of THF/H$_2$O (1:1) and the solvents were removed in vacuo. After removal of the solvents, the deep orange gel was diluted with 30 mL of water and washed with pentane (2×30 mL). The aqueous phase was acidified with solid citric acrd (pH 2). Ethyl acetate was used for extraction. The combined extracts were washed with brine, dried (MgSO$_4$) and concentrated in vacuo. The crude residue was purified by silica gel column chromatography eluting with ethyl ether to afford the desired compound as a yellow oil (5.22 g, 90%); [α]$^{29}$ D-15.7° (c 1.0, MeOH), Lit.$^{14b}$[α]$^{22}$ D-16.9° (c 1.0, MeOH) $^1$H NMR 300 MHz, CDCl$_3$) δ 7.18 & 7.12 (2H, two d), 6.85 (2H,d), 4,58 (1H, two t), 3.80 (3H, s), 3.24 & 3.13 (1H, 2dd), 2.76 & 2.68 (3H, 2s), 1.43 & 1.38 (9H, 2s); FABMS 619.3 (2M+H), 310.2 (M+H), 210.2 (M−Boc); HRFABMS Calcd for C$_{16}$H$_{24}$MO$_5$ (M+H) 310.1654, Found 310.1648.

Cbz-D-MeLeu-Thr(OMe$_2$TyrBoc)-OPac (10).

BocMe$_2$TyrOH (0.27 g, 0.91 mmol) in CH$_2$Cl$_2$ (20 mL), DCC (19.5 mg, 0.95 mmol) and DMAP (41.3 mg) were added at 0° to a solution of Cbz-D-MeLeuThrOPac (0.45 g, 0.91 mmol). The solution was allowed to warm to room temperature and stirred for 12 h. Dicycloheylurea was filtered and washed with ethyl acetate. The filtrate and washings were combined and washed with 10% citric acid, 5% sodium bicarbonate and water, dried over MgSO$_4$ and concentrated. The crude residue was purified by flash column chromatography eluting with hexane and ethyl acetate (4:1) to obtain the product (0.53 g, 74%) as an orange oil; $^1$H NMR (500 MHz, CDCl$_3$δ 7.30–8.00(10H,m), 6.82 & 7.10 (2H, d), 5.31(1H, s), 5.20–4.8.5(1H, m), 3.74(3H, s), 3.10 & 3.07(1H, 2 dd) 2.92(3H, s), 2.73 (3H, s), 1.71 (3H, d), 1.44 & 1.37 (9H, 2 s), 0,92 (6H, m); FABMS 828.4 (M+K), 812.4 (M+Na), 790.3 (M+H), 690.4 M−Boc); HRFABMS Calcd for D$_{43}$H$_{57}$N$_3$O$_{11}$ (M+H) 790.3915, Found 790.3916.

Cbs-D-MeLeu-Thr(OMe$_2$TyBoc)-OH (5).

The tripeptide 10 (30.0 mg, 38.0 μmol) was treated with Zn (60 mg) in AcOH/H$_2$O (70:30) and the mixture was stirred at rt overnight, Zn was filtered off using celite and the solution was partitioned between ether and water. The organic layer was separated and dried over Na$_2$SO$_4$. Purification by reversed phase column chromatography (CH$_3$CH/H$_2$O gradient system) afforded the product as a clear oil (21.3 mg, 92%); FABMS 710.4 (M+K), 694.3 (M+Na), 672.3 (M+H), 572.3 (M−Boc), see FIG. 1; HRFABMS Calcd for C$_{35}$H$_{52}$N$_4$O$_9$ (M+H) 672.3734, Found 672,3674.

Methyl (2S,3S)-2-Hydroxy-3-methylpentanoate.

Acetyl chloride (6.13 mL) was added dropwise to MeOH (90 mL) cooled in an ice bath. After addition was complete, a solution of the α-hydroxy acid (23.0 g, 0. 17 mol) in MeOH (60 mL) was added. The solution was stirred at 0° C. for 1 h, then at rt oversight, concentrated and diluted with ether. The either solution was washed with saturated NaHCO$_3$, brine, bried over MgSO$_4$ and concentrated to give a yellow oil (19.8 g, 80%); [α]$^{29}$D+27.3 (c 0.95, CHCl$_3$), Lit.$^{18}$[λ]$^{20}$D+28.5(c 0.95, CHCl$_3$); $^1$H NMR(300 Mhz, CDCl$_3$) δ 0.91 (t, 3H), 0.97 (d, 3H), 1.21 & 1.37 (m, 2H), 1.78 (m,1H), 2.92 (br s, 1H), 3.82 (s, 3H), 4.08 (d, 1H); CIMS 147.1 (M+H).

Methyl (2S, 3S)-2-Tosyloxy-3-methylpentanoate(13).

The hydroxypentanoate (4.44 g, 30.6 mmol) was dissolved in dry CH$_2$Cl$_2$ and cooled in an ice bath to 0° C. Pyridine (45.0 mL) was added followed by p-toluenesulfonyl chloride (11.5 g, 60.8 mmol) in small portions with constant stirring. The mixture was stirred at rt overnight, then heated at 40° C. for 1 h. The solvent was evaporated and the residue dissolved in EtOAc and washed with 1N H$_2$SO$_4$ and 1N KHCO$_3$. The extracts were dried over MgSO$_4$ and evaporated in vacuo to give a dark orange oil (8.32 g, 88%); $^1$H NMR (300 MHz, CDCl$_3$) δ 0.93 (t, 3H), 0.97 (d, 3H), 1.21 & 1.41 (m, 1H), 1.91 (m, 1H), 2.41 (s, 2H), 3.60 (s, 3H), 4.63 (d, 2H), 7.24 & 7.80 (d, 2H); FABMS 339.2 (M+K), 323.2 (M+Na), 301.1 (M+H), 241.2 (M−CO$_2$CH$_3$); HRFABMS Calcd for C$_{14}$H$_{21}$O$_5$S (M+H) 301.11 10, Found 301.1109.

Methyl (2R, 3S)-2-Azido-3-methylpentanoate (14).

Sodium azide (1.20 g, 18.6 mmol) was added to a stirred solution of methyl 2-tosyloxy-3-methylpentanoate (3.29 g, 10.9 mmol) in DMF (30 mL). The solution was kept at 50° C. for 24 h, then partitioned between EtOAc and water. The aqueous layer was separated and extracted with EtOAc (3×50 mL). The combined organic layers were dried over $MgSO_4$ and concentrated in vacuo to give a deep yellow oil (1.51 g, 81%), IR (neat) v 3500–3000 (very br m), 2970 (s), 2939 (br m), 2111 (s), 1736 (s), 1472 (w), 1387 (w), 1225 (br m), 1175 (w), 1086 (w), 732 (s) $cm^{-1}$; $^1H$ NMR (300 MHz, $CDCl_3$) δ 0.93 (t, 3H), 0.97 (d, 3H), 1.22 & 1.43 (m, 1H), 1.96 (m, 1H), 3.78 (s, 3H), 3.85 (d, 2H); CIMS 172.1 (M+H).

(2R, 3S)-2-Azido-3-methylpentanoic acid (15).

To a solution of a α-azido ester (6.56 g, 38.3 mmol) in THF (58 mL) at 0° C. was added 1N NaOH (52 mL). The reaction mixture was stirred at 0° C. for 1 h and then at rt overnight. The mixture was diluted with ether (30 mL), the organic layer separated, and the aqueous phase extracted with ether (30 mL). The aqueous layer was then cooled to 0° C., acidified to pH 2 by dropwise addition of conc. HCl, and extracted with ethyl acetate (3×25 mL). The combined ethyl acetate extracts were dried ($MgSO_4$) and concentrated in vacuo to furnish 10.9 g (95%); IR (neat) $v_{max}$3500–3000 (very br m), 2974 (s), 2942 (br m), 2090 (s), 1464 (w), 1382 (w), 1222 (br m), 1168 (w), 1088 (w), 721 (s) $cm^{-1}$; $^1H$ NMR (300 MHz, $CDCl_3$) δ 0.93 (3H, t), 0.97 (3H, d), 1.21 & 1.41 (1H, m), 1.97 (1H, m), 3.90 (2H, m); FABMS 158.2 (M+H); HRFABMS Calcd for $C_{14}H_{21}O_5S$ (M+H),301.1110, Found 301.1109.

D-allo-isoleucine (16).

To a solution of the α-azido acid (6.01 g, 38.2 mmol) in MeOH (25 mL) was added 20% $Pd(OH)_2$ on carbon (1.89 g). The reaction flask was purged with $H_2$ gas and the contents vigorously stirred at rt and atmospheric pressure for 15 h, filtered and the filter pad washed with distilled water and ethanol. The filtrate was concentrated in vacuo to afford the product as a white solid. Recrystallization from EtOAc provided the compound as colorless needles (4.75 g, 95%); $^1H$ NMR (300 MHz, MeOH-$d_4$) δ 0.93 (t, 3H), 0.97 (d, 3H), 1.32 & 1.46 (m, 1H), 2.47 (m, 1H), 3.58 (d, 2H); FABMS 132.1 (M+H); Anal. Calcd for $C_6H_{13}NO_2$: C, 54.92; H, 9.99; N, 10.64. Found: C, 54.79; H, 10.17; N, 10.26

N-tert-Butoxycarbonyl-D-allo-isoleucine (17).

A solution of D-allo-isoleucine (120 mg, 0.916 mmol) was dissolved in water (2.5 mL) and 1N NaOH (1.83 mL) and stirred at rt for 48 h. Di-tert-butyl dicarbonate (200 mg, 0.916 mmol) in dioxane (5,00 mL) was added to the stirred mixture at 0° C. After 12 h the dioxane was evaporated, the aqueous residue washed with $Et_2O$, mixed with EtOAc, and the rapidly stirred mixture acidified with 2 N $H_2SO_4$ at 0° C. This solution was extracted with EtOAc. and the combined organic extracts were dried ($Na_2SO_4$) and coned in vacuo to a crystalline material (179 mg, 85%); mp 35–37° C. (Lit.[28] 34–36° C.); $[α]^{29}D$ -42.7° (c 2.04, $CHCl_3$), [Lit.[28] $[α]^{27}D$-40.7° (c 2.06, $CHCl_3$]); $^1H$ NMR (300 MHz. $CDCl_3$) δ 5.52 (br s, 1H), 3.72–3.54 (m, 1H), 1.92–2.01 (m, 1H), 1.43 (s, 9H). 1.37–1.12 (m, 3H), 0.97 (t, 3H), 0.93 (d, 3H); FABMS 463.2 (2M+H), 232.1 (M+H), 132.1 M−Boc); HRFABMS Calcd for C: $_1H_{21}NO_4$(M+H) 232.1551, Found 232.1548.

Ethyl Hydrogen Malonate.

A previously reported procedure was used.[29] Potassium hydroxide (10.02 g, 85% KOH, 156 mmol) in ethanol (99 mL) was added dropwise to a stirred solution of diethyl malonate (23.69 mL, 156 mmol) in ethanol (108 mL), and the solution was stirred at rt overnight. The mixture refluxed for 1 h and the solid was filtered off. The ethanolic solution on cooling gave the monopotassium salt. Water (5 mL) was added to the dried potassium salt, and the solution was cooled to 0° C. Concentrated hydrochloric acid (3.45 mL) was added, keeping the temperature below 5° C. The solid was filtered and washed with ether. The filtrate was extracted with $CH_2Cl_2$, dried ($MgSO_4$), and concentrated to give a yellow oil (9.96 g, 48%; Lit.[29b] 51%); $^1H$ NMR (300 MHz, $CDCl_3$) δ 4.37 (s, 2H), 4.24 (q, 2H), 1.34 (t, 3H); FABMS 133.0 (M+H).

Ethyl (4R,5S)-3-tert-Butoxycarbonylamino-5-methyl-3-oxoheptanoate (18).

A tetrahydrofuran solution of isopropylmagnesium chloride (1.42 mL, 13.5 mmol) was added dropwise to a solution of ethyl hydrogen malonate (891 mg, 6.75 mmol) in dry $CH_2Cl_2$ (5.62 mL). The reaction was then cooled in an ice-salt bath while a solution of Boc-D-allo-isoleucine (520 mg, 2.25 mmol) and N,N'-carbonyldiimidazole (360 mg, 2.25 mmol) in dry THF (1.20 mL) was added. The mixture was stirred overnight at rt, then poured into cold hydrochloric acid (10%, 100 mL). The ethyl ester was extracted with ether, washed with aqueous $NaHCO_3$, dried ($MgSO_4$) and concentrated to give 475 mg (70%) of a pale yellow oil; IR (neat) $v_{max}$ 3355, 1750, 1700$cm^{-1}$; $^1H$ NMR (300 MHz, $CDCl_3$) δ 4.98 (d, 1H), 3.90–4.57 (m, 1H), 4.18 (q, 2H), 3.46 (s, 2H), 0.70–2.00 (m, 6H), 1.43 (s, 9H), 1.26 (t, 3H), 0.78 (d, 3H); FABMS 302.2 (M+H), 202.2 (M−Boc).

(3S, 4R, 5S)-N-tert-Butoxycarbonyl-isostatine Ethyl Ester (19a).

To a stirred solution of 18 (500 mg, 1.66 mmol) in $Et_2O$ (2.90 mL) and EtOH (6.80 mL) cooled in an ice-salt bath was added $NaBH_4$ (60 mg, 1.58 mmol). The solution was allowed to stir at −20° C. for 2 h then poured into ice water. extracted with EtOAc and dried over $MgSO_4$. The residue was chromatographed on silica gel (hexane/EtOAc=4/1) to give 325 mg (65%) of the desired isomer 19a and 25 mg (5%) of the minor isomer 19b. 19a: $R_f$0.20 (hexane/EtOAc= 3/1); $[α]^{29}D$-6.7° (c.0.5, MeOH), Lit.[30] $[α]^{23}D$-6.4° (c 0.5, MeOH); IR (neat) $v_{max}$3350, 1740, 1700 $cm^{-1}$; $^1H$ NMR (300 MHz, $CDCl_3$) δ 4.43 (d, 1H), 4.20 (q, 2H), 3.90–3.61 (m, 2H), 3.30 (br s, 1H), 2.50 (d, 2H), 1.90–1.98 (m, 1H), 1.41–1.30 (m, 2H), 1.40 (s, 9H), 1.24 (t, 3H), 0.97 (d, 3H), 0.90 (t, 3H); FABMS 304.2 (M+H) 204.2 (M−Boc); HRFABMS Calcd for $C_{15}H_{29}NO_5$ (M+H) 304.2117, Found 304.2123; Anal. Calcd for $C_{15}H_{28}NO_5$: C, 59.37; H, 9.64; N, 4.62. Found: C, 59.03; H, 9.38; N, 4.88. 19b: $R_f$ 0.22 (hexane/EtOAc=3/1); $[α]^{29}D$+26.9 (c 0.5, MeOH), Lit.[30] $[α]^{23}D$+26.4 (c 0.5, MeOH); IR (neat) $v_{max}$ 3410, 1740, 1710.$cm^{-1}$ $^1H$ NMR (300 MHz, $CDCl_3$) δ 4.42 (d, 1H), 4.20 (q, 2H), 3.87–3.61 (m, 2H), 3.32 (br s, 1H), 2.49 (d, 2H), 1.92–1.98 (m, 1H), 1.41–1.30 (m, 2H), 1.40 (s, 9H), 1.24 (t, 3H), 0.98 (d, 3H), 0.88 (t, 3H); FABMS 304.2 (M+H), 204.2 (M−Boc); HRFABMS Calcd for $C_{15}H_{29}NO_5$ (M+H) 304.2117, Found 304.2123; Anal. Calcd for $C_{15}H_{28}NO_5$: C, 59.37; H, 9.64; N, 4.62. Found: C, 59.03; H, 9.38; N, 488.

(3S, 4R, 5S)-N-tert-Butoxycarbonyl-isostatine (20).

Boc-(3S, 4R, 5S)-Ist-OEt (300 mg, 1.00 mmol) was dissolved in methanol (5.00 mL) and 2N NaOH (2.00 mL) was alowly added to the mixture at 0° C. The solution was stirred at rt overnight at which time TLC analysis (hexane/EtOAc=4/1) showed the presence of a carboxylic acid. The mixture was neutralized using 2N HCl. The solvent was evaporated and the solution was partitioned between EtOAc and water and the organic layer separated. Aqueous HCl was added to the aqueous layer to pH 3. This was extracted with EtOAc and the EtOAc extracts were combined. The solution was dried over $MgSO_4$ and the solvent evaporated to give a yellow oil (215 mg, 78%) which was used for the next reaction without purification; $[\alpha]^{29}D -4.6°$ (c 0.0014, CHCl$_3$), Lit.[11b][$\alpha$]$^{20}$D -57° (c 0.0014, CHCl$_3$); $^1$H NMR (300 MHz, CDCl$_3$) 4.43 (d, 1H), 3.85–3.63 (m,2H), 2.76 (br, 1H), 2.41 (m, 2H), 2.00–1.93 (m, 1H), 1.43–1.35 (m, 2H), 1.43 (s, 9H), 0.91 (t, 3H), 0.87 (d, 3H); FABMS 276.1 (M+H), 176.1(M–Boc); HRFABMS Calcd for C$_{13}$H$_{25}$NO$_5$ (M+H) 276.1806, Found 276.1810.

Ethyl Hydrogen Methylmalonate.

Potassium hydroxide (3.53 g, 90% KOH, 57.4 mmol) in ethanol (35 mL) was added dropwise to a stirred solution of diethyl methylmalonate (9.87 mL, 57.4 mmol) in ethanol (40 mL), and the solution was stirred at rt overnight. The mixture was heated at reflux for 1 hr and the solid filtered off. The ethanolic solution on cooling gave the monopotassium salt. Water (5 mL) was added to the dried potassium salt, and the solution was cooled to 0° C. Concentrated hydrochloric acid (3.45 mL) was added, keeping the temperature below 5° C. The solid was filtered and washed with ether and the filtrate was extracted with CH$_2$Cl$_2$, then dried and concentrated to give a yellow oil (4.86 g, 58%, Lit.$^{29}$ 60%); $^1$H NMR (200 MHz, CDCl$_3$) δ 4.23 (q, 2H), 3.47 (q, 1H), 1.42 (d, 3H), 1.27 (t, 3H); FABMS 147.1 (M+H).

Cbz-AipOEt (22).

A tetrahydrofuran solution of isopropylmagensium chloride (9.57 mL, 90.8 mmol) was added dropwise to a solution of ethyl hydrogen methylmalonate (6.63 g, 45.4 mmol) in dry CH$_2$Cl$_2$ (35 mL). The reaction was then cooled in an ice-salt bath while a solution of Cbz-L-valine (3.87 g, 15.1 mmol) and N,N'-carbonyldiimidazole (2.44 g, 15.1 mmol) in dry THF (15 mL) was added. The mixture was stirred overnight at rt, then poured into cold hydrochloric acid (10%, 200 mL). The ethyl ester was extracted with ether, washed with aqueous NaHCO$_3$, brine, dried (MgSO$_4$) and concentrated. Purification by flash column chromatography (hexane/EtOAc=10/1) gave the desired product as a yellow oil (4.50 g, 89%); $^1$H NMR (200 MHz, CDCl$_3$) δ 7.32–7.38 (s, 5H), 5.24–5.37 (m, 1H), 5.17 (s, 2H), 4.20 (q, 2H), 3.41 (q, 1H), 218–2.21 (m, 1H), 1.45 (d, 3H), 1.32–1.37 (m, 1H), 1.24 (t, 3H), 0.94 (d, 3H), 0.81 (d, 3H); FABMS 374.0 (M+K), 336.1 (M+H), 292.1 (M–OEt); HRFABMS Calcd for C$_{18}$H$_{26}$NO$_5$ (M+H) 336.1811, Found 336.1817; Anal. Calcd for C$_{18}$H$_{25}$NO$_5$: C, 64.44; H, 7.52; N, 4.18. Found: C, 64.70; H, 7.62; N, 4.37.

Cbz-DihydroAipOEt.

To a stirred solution of Cbz-AipOEt (6.54 g, 19.5 mmol) in Et$_2$O (15 mL) and EtOH (35 mL) at −20° C., NaBH$_4$ (0.74 g, 19.5 mmol) was added over a period of 15 min. The reactioin mixture was stirred 15 min at −20° C. and poured into ice water (50 mL). After extraction with ethyl acetate (30 mL), the combined organic extracts were dried (MgSO$_4$) and concentrated to give a yellow oil (6.12 g, 93%); $^1$H NMR (300 MHz, CDCl$_3$) δ 7.39 (s, 5H), 7.01 (br s, 1H), 5.13 (s, 2H), 4.72–4.53 (m, 1H), 4.18 (q, 2H), 3.80–3.71 (m, 1H), 3.38 (br s, 1H), 2.32–2.20 (m, 1H), 1.98 (m, 1H), 1.40 (d, 3H), 1.25 (t, 3H), 9.92–0.80 (m, 6H); FABMS 338.1 (M+H); Anal. Calcd for C$_{18}$H$_{27}$NO$_5$: C, 64.06; H, 8.07; N, 4.15. Found : C, 64.21; H, 8.36; N, 4.29.

Cbz-DihydorAipOH.

Cbz-DihydroAipOEt (5.99 g, 17.7 mmol) was dissolved in methanol and 2N KOH was slowly added to the mixture at 0° C. The solution was allowed to stir for 2 h. TLC analysis (hexane/ethyl acetate 10:1) showed the reaction to be complete. At this time, 2N HCl was added to neutralization. The solvent was evaporated and the solution was partitioned between ethyl acetate and water. The organic layer was separated. Aqueous HCl was added to bring the aqueous layer to pH 3 which was then extracted with ethyl acetate. The ethyl acetate extracts were combined, the solution was dried over MgSO$_4$ and the solvent was evaporated to give a pale yellow oil (4.59 g, 84%); $^1$H NMR (300 MHz, CDCl$_3$) δ 7.39 (s, 5H), 7.04 (br s, 1H), 5.13 (s, 2H), 4.40–4.20 (m. 1H), 3.92–3.71 (m, 1H), 3.33 (br s, 1H), 2.32–2.20 (m, 1H), 1.98 (m, 1H), 1.40 (d, 3H), 0.92–0.80 (m, 6H); FABMS 310.2 (M+H); HRFABMS Calcd for C$_{16}$H$_{24}$NO$_5$ (M+H) 310.1654, Found 310.1651; Anal. Calcd for C$_{16}$H$_{23}$NO$_5$: C, 62.10; H, 7.51; N, 4.53. Found : C, 62.50; H, 7.71; N, 4.37.

Cbz-DihydroAip-LeuOMe (23). Cbz-DihydroAipOH (1.17 g, 3.82 mmol) was dissolved in dry CH$_2$Cl$_2$ (25 mL) and cooled to 0° C. DDC (0.87 g, 4.20 mmol) and DMAP (0.32 g, 2.90 mmol) were added with stirring and the mixture was stirred for 1 h. After filtration of dicycloheylurea, leucine methyl ester (0.56 g, 3.82 mmol) was added and the mixture was stirred overnight. The residue was concentrated and taken up in ethyl acetate. The solution was washed with aqueous citric acid, aqueous sodium bicarbonate, dried over MgSO$_4$, and concentrated. The residue was purified by column chromatography eluting with hexane/ethyl acetate (50:50) to give a clear oil (1.23 g, 74%); $^1$H NMR (300 MHz, CDCl$_3$) δ 7.43 (s, 5H), 6.81 (br s, 1H), 6,42 (br s, 1H), 4.78–4.72 (m, 1H), 4.48–4.43 (m, 1H), 3.78–3.72 (m, 1H), 3.67 (s, 3H), 3.51 (br s, 1H), 2.50–2.40 (m, 1H), 2.37–2.20 (m, 1H), 1.40–1.30 (dd, 6H), 1.10–0.90 (m. 9H), FABMS 437.2 (M+H); HRFABMS Calcd for C$_{23}$H$_{37}$N$_2$O$_6$ (M+H) 437.2652, Found 437.2653; Anal. Calcd for C$_{23}$H$_{36}$N$_2$O$_6$: C, 63.27; H, 8.32; N. 6.42. Found: C, 63.65; H, 8.35; N, 6.49.

Cbz-DihydroAip-LeuOH.

Cbz-DihydroAip-LeuOMe (303 mg, 0.70 mmol) was dissolved in MeOH and 2N KOH was slowly added with cooling. After approximately 3 h stirring, TLC analysis (hexane/ethyl acetate 6:1) showed reaction to be complete. The solution was neutralized with 2N HCl and extracted with ethyl actate. The aqueous layer was adjusted to pH 3 and extracted with ethyl acetate. The combined ethyl acetate extracts were then dried over MgSO$_4$. Evaporation of the solvent left a yellow oil (270 mg, 92%); $^1$H NMR (200 MHz, CDCl$_3$) δ 7.42 (s, 5H), 6.81 (br s, 1H), 6.42 (br s 1H), 4.78–4.72 (m, 1H), 4.48–4.42 (m, 1H), 3.78–3.72 (m, 1H), 3.51 (br s, 1H), 2.50–2.40 (m, 1H), 2.37–2.30 (m, 1H), 1.40–1.30 (dd, 6H), 1.10–0.90 (m, 9H); FABMS 423.2 (M+H); HRFABMS Calcd for C$_{22}$H$_{35}$N$_2$O$_6$ (M+H) 423.2495, Found 423.2493.

Cbz-DihydroAip-Leu-OPac.

Cbz-DihydroAip-LeuOH (2.03 g, 4.81 mmol) was dissolved in ethyl acetate (33 mL), triethylamine (0.66 mL) and phenacyl (Pac) bromide (0.97 mg, 6.85 mmol) were added to the mixture was stirred at rt overnight. Water and ether were added and the two layers separated. The organic layer was washed with 0.1N HCl saturated sodium bicarbonate, and brine, then dried over MgSO$_4$. Concentration by evaporation of the solvent gave a tan oil. The residue was chromatographed on silica gel (hexane/EtOAc=4/1) to give 1.27 g (53%) of one isomer and 0.96 g (40%) of the other isomer; a: R$_f$ 0.46 (hexane/EtOAc=1/1); $^1$H NMR (300 MHz, CDCl$_3$) δ 7.90 (d, 2H), 7.61 (m, 1H), 7.50 (m, 2H), 7.40 (s, 5H), 6.03 (br s, 1H), 6.00 (br s, 1H), 5.40 (AB q, 2H), 5.10 (s, 2H), 4.78–4.72 (m, 1H), 4.45–4.53 (m, 1H), 4.05–4.10 (m, 1H), 3.70 (br s, 1H), 2.50 (q, 1H), 2.40–2.32 (n, 1H), 2.00–1.85 (m, 3H), 1.25 (dd, 6H), 1.06 (d, 3H), 1.02–0.80 (dd, 6H); FABMS 541.2 (M+H); HRFABMS Calcd for C$_{30}$H$_{41}$N$_2$O$_7$ (M+H) 541.2916, Found 541.2916; Anal. Calcd for C$_{30}$H$_{40}$N$_2$O$_7$: C, 66.63; H, 7.46; N, 5.18. Found: C, 66.61; H, 7.44; N, 5.26. b: R$_f$ 0.30 (hexane/

EtOAc=1/1); $^1$H NMR (300 MHz, CDCl$_3$) δ 7.90 (d, 2H), 7.62 (m, 1H), 7.50 (m, 2H), 7.40 (s, 5H), 6.03 (br s, 1H), 6.00 (br s, 1H), 5.40 (AB q, 2H), 5.10 (s, 2H), 4.78–4.73 (m, 1H), 4.44–4.55 (m, 1H), 4.06–4.12 (m, 1H), 3.72 (br s, 1H), 2.51 (q 1H), 2.39 –2.31 (m, 1H), 2.00–1.85 (m, 3H), 1.24 (dd, 6H), 1.06 (d. 3H), 1.05–0.83 (dd, 6H); FABMS m/z 541.2 (M+H); HRFABMS Calcd for C$_{30}$H$_{41}$N$_2$O$_7$ (M+H) 541.2916, Found 541.2914; Anal. Calcd for C$_{30}$H$_{40}$N$_2$O$_7$: C, 66.63; H, 7.46; N, 5.18. Found: C, 66.61; H, 7.44; N, 5.26.

Cbz-Aip-Leu-OPac (24).

A solution of Cbz-Dihydro-Aip-LeuO-Pac (0.44 g, 0.81 mmol) in CH$_2$Cl$_2$ (2.10 mL) was stirred while pyridinium chlorochromate on alumina reagent[16] (1.57 g) was added. After 2 h stirring at rt, the solution was filtered and washed with ether. The combined filtrates were combined and the solvent evaporated. The residue was chromatographed on silica gel hexane/EtOAc=4/1) to give 0.37 g (87%) of the desired product as a white solid; R$_f$ 0.42 hexane/EtOAc=1/1); $^1$H NMR (300 MHz, CDCl$_3$) δ 7.90 (d, 2H), 7.61 (m, 1H), 7.50 (m, 2H), 7.40 (s, 5H), 6.90 (br s, 1H), 6.88 (br s, 1H), 5.40 (AB q, 2H), 5.18 (s, 2H), 4.78–4.72 (m, 1H), 4.45–4.53 (m, 1H), 3.68 (q, 1H), 2.25–2.38 (m, 1H), 1.92–1.71 (m, 3H), 1.45 (d, 3H), 1.10–1.00 (dd, 6H), 0.80–0.75 (dd, 6H); FABMS 1077.3 (2M+H), 577.3 (M+K), 561.2 (M+Na), 539.3 (M+H); HRFABMS Calcd for C$_{30}$H$_{39}$N$_2$O$_7$ (M+H) 539.2757, Found 539.2762; Anal. Calcd for C$_{30}$H$_{38}$N$_2$O$_7$: C, 66.88; H, 7.11; N, 5.18. Found: C, 66.92; H, 7.33; N, 478.

Cbz-Aip-Leu-OH.

The protected dipeptide (167 mg, 0.31 mmol) was treated with Zn (500 mg) in AcOH/H$_2$O (70:30). The mixture was allowed to stir at rt overnight, Zn was filtered off using celite and the solution was partitioned between ether and water. The organic layer was separated and dried over Na$_2$SO$_4$. Purification by column chromatography (CHCl$_3$/MeOH) afforded the product as a white powder. The reaction flask was protected with a CaCl$_2$ tube and the mixture allowed to stir at rt for 1½ h. Solvent was evaporated and the remaining oil was placed under vacuum to give a yellow solid (87.7 mg, 70%); $^1$H NMR (300 MHz, CDCl$_3$) δ 7.42 (s, 5H), 6.88 (br s, 1H), 6.85 (br s, 1H), 5.42 (AB q, 2H), 5.15 (s, 2H), 4.79–4.72 (m, 1H), 4.55–4.47 (m, 1H), 3.67 (q, 1H), 2.37–2.26 (m, 1H), 1.94–1.75 (m, 3H), 1.46 (d, 3H), 1.12–1.01 (dd, 6H), 0.80–0.74 (dd, 6H); FABMS 460.3 (M+K), 443.2 (M+Na), 421.3 (M+H).

Cbz-Aip-Leu-Pro OTMSe.

Cbz-Aip-Leu-OH (36.7 mg, 85.0 μmol) was dissolved in dry CH$_2$Cl$_2$ (1.0 mL) and the solution was cooled to 0° C. DCC (26.1 mg, 0.13 mmol) was added and the mixture was stirred for 30 min at 0° C. Pro-OTMSe (18.5 mg, 85.0 μmol) in CH$_2$Cl$_2$ (1.0 mL) was added and the solution was stirred for 30 min at 0° C. and at rt overnight. The residue was concentrated and taken up in ethyl acetate. The solution was washed with aqueous citric acid, aqueous sodium bicarbonate, dried over MgSO$_4$, and concentrated. The residue was purified by column chromatography, eluting with CH$_2$Cl$_2$/MeOH (95:5) to give a yellow oil (34.0 mg, 65%); $^1$H NMR (300 MHz, CDCl$_3$) δ 7.47 (s, 5H), 6.85 (br s, 1H), 6.84 (br s, 1H), 5.45 (AB q, 2H), 5.13 (s 2H), 4.80–4.73 (m, 1H), 4.53–4.47 (m, 1H), 4.24–4.01 (dt, 4H), 3.63 (q, 1H), 2.35–2.23 (m, 1H), 1.94–1.75 (m, 3H), 1.46 (d, 3H), 1.12–1.01 (dd, 6H), 0.80–0.74 (dd, 6H), 0.00 (s, 9H); FABMS 656.3 (M+K), 640.2 (M+Na), 618.3 (M+H).

H-Aip-Leu-Pro-OTMSe.

The protected tripeptide (24.9 mg, 40.3 μmol) was dissolved in isopropyl alcohol (1.00 mL) and 10% Pd/C catalyst (0.99 mg) was added. The solution was hydrogenated for 3 h, the catalyst was removed by filtration over celite, and the solvent removed to afford the desired product (15.6 mg. 82%). $^1$H NMR (300 MHz, CDCl$_3$) δ 6.84 (br s, 1H). 6.82 (br s, 1H), 5.41 (AB q, 2H), 5.09 (s, 2H), 4.82–4.71 (m, 1H), 4.56–4.48 (m, 1H), 4.25–4.00 (dt, 4H), 3.62 (q, 1H), 2.37–2.23 (m, 1H), 1.95–1.75 (m, 3H), 1.47 (d, 3H), 1.14–1.01 (dd, 6H), 0.82–0.74 (dd, 6H), 0.00 (s, 9H); FABMS m/z 506.3 (M+Na); 484.3 (M+H).

Bos-Ist-Aip-Leu-Pro-OTMSe.

Boc-Ist-OH (7.51 mg, 27.3 μmol) was dissolved in dry CH$_2$Cl$_2$ (1.0 mL) and the solution was cooled to 0° C. DCC (10.52 mg, 0.089 mmol) was added and then mixture was stirred for 30 min at 0° C. H-Aip-Leu-Pro-OTMSe (3.28 mg, 27.3 μmol) in CH$_2$Cl$_2$ (1.0 mL) was added and the solution was stirred for 30 min at 0° C. and at rt overnight. The residue was concentrated and taken up in ethyl acetate. The solution was washed with aqueous citric acid, aqueous sodium bicarbonate, dried over MgSO$_4$, and concentrated. The residue was purified by reversed phase HPLC using a gradient system of CH$_3$CH/H$_2$O (45.0 mg, 83%); FABMS 741.5 (M+H), 641.5 (M–Boc).

H-Ist-Aip-Leu-Pro-OTMSe (6).

Figure 2:
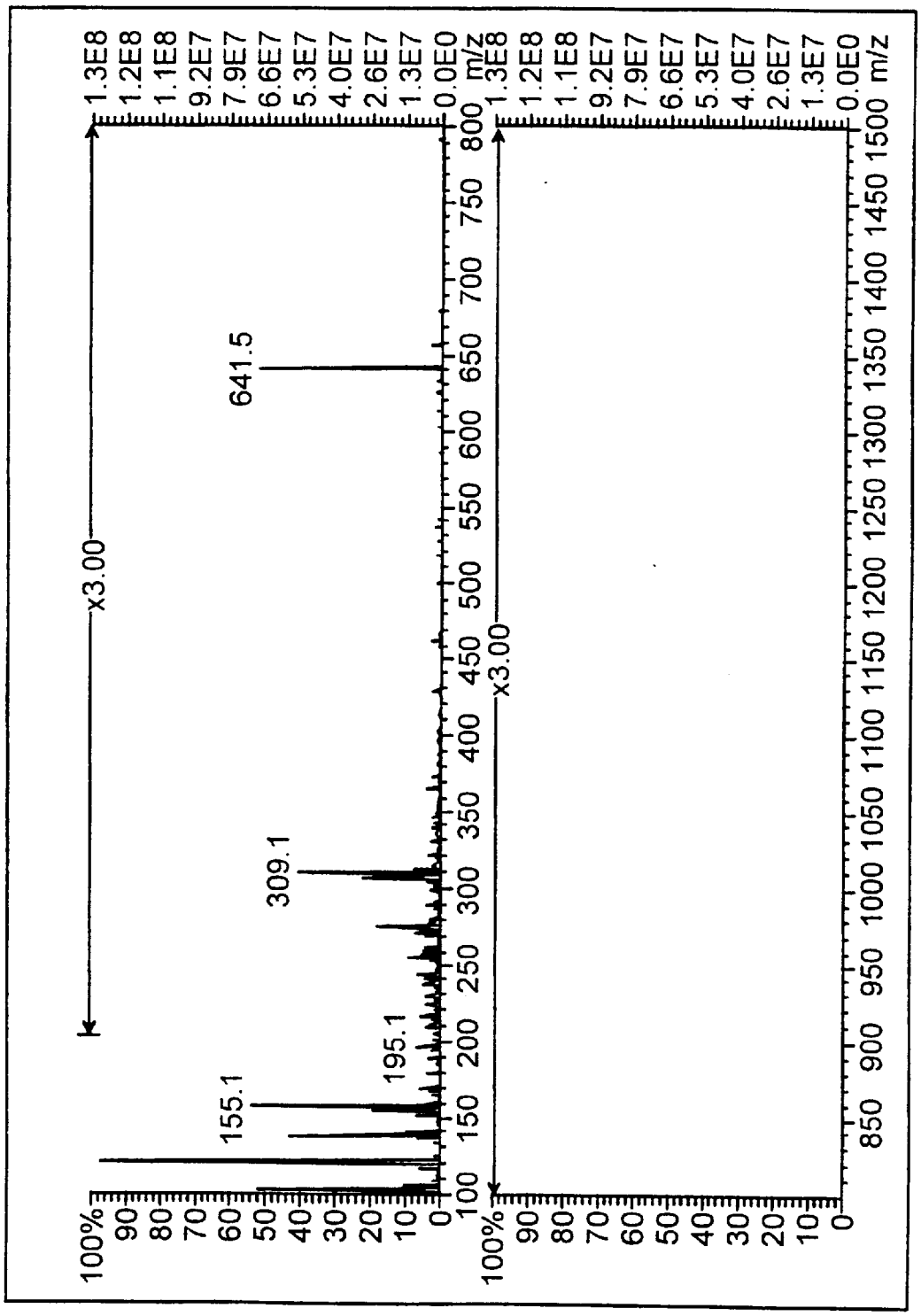
FIG. 2 is a LRFAB mass spectrum of deprotected tripeptide (6).

The protected tetrapeptide (30.0 mg, 0.045 mmol) was dissolved in MeOH (2 mL) and a steady current of HCl was passed through the solution for approximately 20 min. Evaporation of the solvent produced a yellow oil which was purified by reversed phase column chromatography eluting with CH$_3$CN/H$_2$O (gradient system) to give 22.0 mg (87%) of the compound as a yellow powder; FABMS 641.5 (M+H), see FIG. 2.

Cbz-D-MeLeu-Thr[O-N,O—Me$_2$TyrBoc)]-Ist-Aip-Leu-Pro-OTMSe (4).

Figure 3:
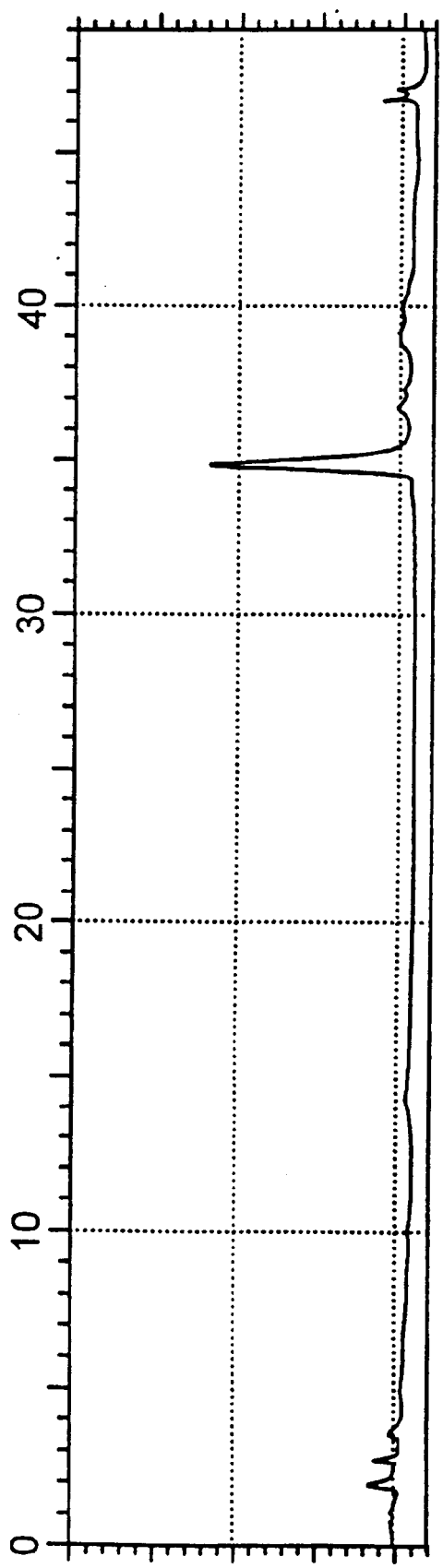
FIG. 3 is a reversed phase HPLC trace of the fully protected heptapeptide (4).
Figure 4:
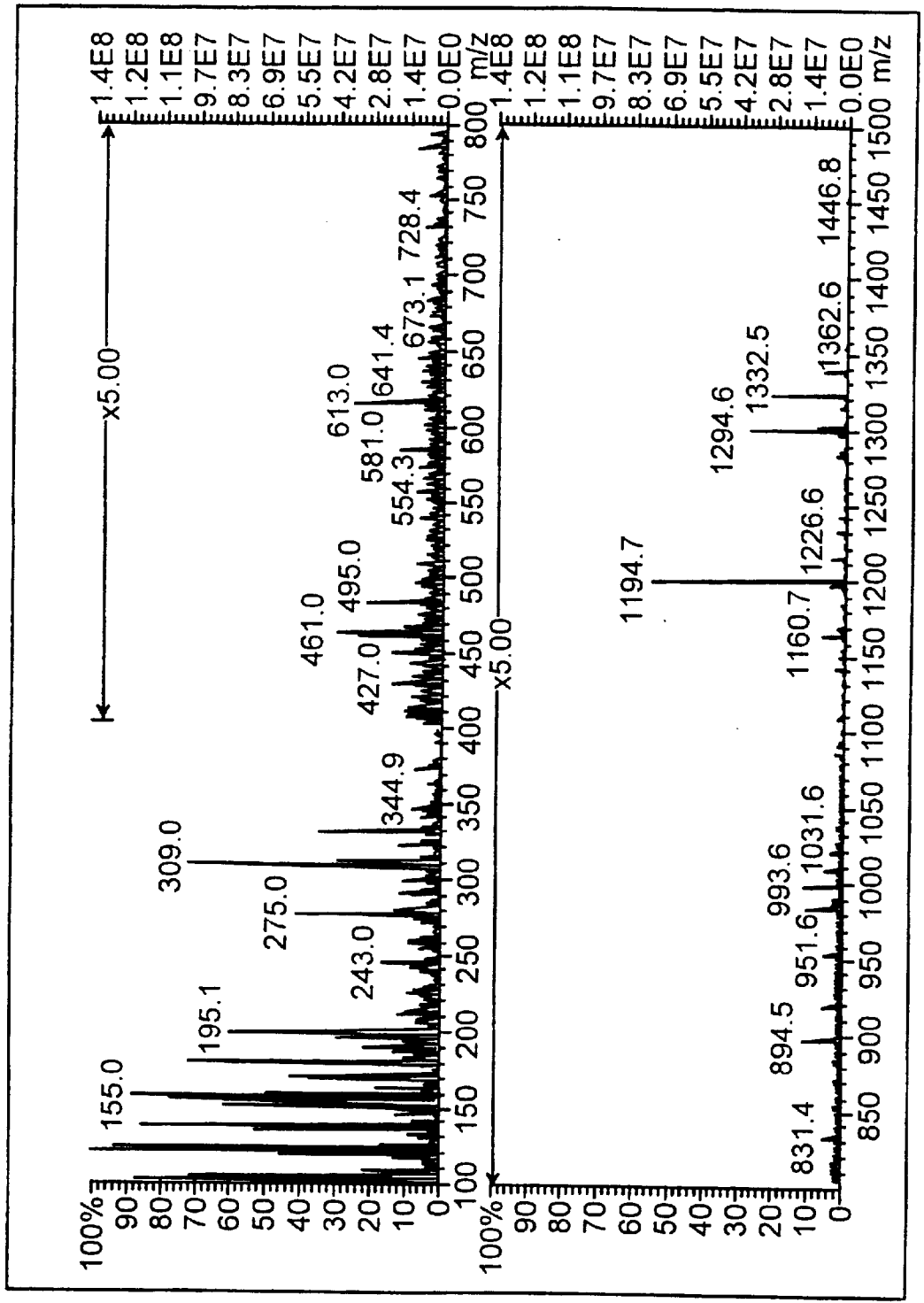
FIG. 4 is a LRFAB mass spectrum of the fully protected heptapeptide (4).

Acid 5 (21.9 mg, 28.4 μmol) and N-methylmorpholine (6.4 μL) were dissolved in dry THF (0.4 mL), and the solution was cooled to 0° C. A solution of amine 6 (16.2 mg, 28.4 μmol) and HOBT (0.81 mg) in 1.5 mL of the dry THF were added. This suspension was mixed with a cold solution of EDCI (9.76 mg, 51.1 μmol) in 0.5 mL of THF. The reaction mixture was stirred at 0° C. for ½ h. The solution was then concentrated to 0.50 mL, kept at 0° C. for 24 h, then diluted with ether. The organic layer was washed with 10% HCl, 5% NaHCO$_3$, and saturated NaCl solutions. The organic layer was dried (Na$_2$SO$_4$), filtered, and concentrated. The crude oil was purified by reversed phase HPLC using a gradient system of CH$_3$CN/H$_2$O to give 11.6 mg (32%) of the linear heptapeptide, see FIG. 3; FABMS 1294.2 (M+H); 1194/2 (M–Boc), see FIG. 4; HRFABMS Calcd for C$_{67}$H$_{108}$N$_7$O$_{16}$Si (M+H) 1294.7649, Found 1294.7644.

Cbs-D-MeLeu-Thr-N,O—MeTyr-Ist-Aip-Leu-ProOH (7).

Figure 5:
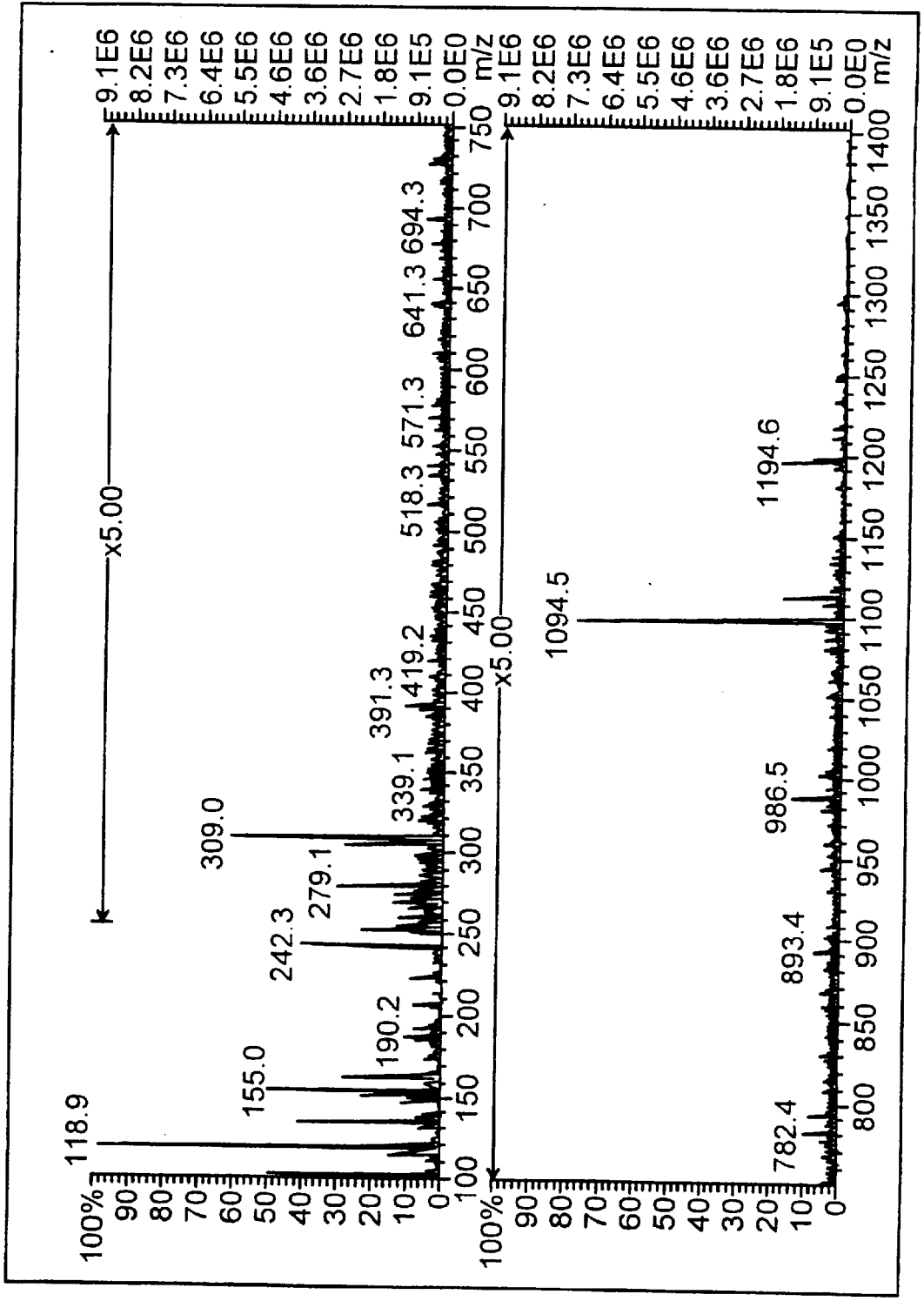
FIG. 5 is a LRFAB mass spectrum of fully deprotected heptapeptide (4).
Figure 6:
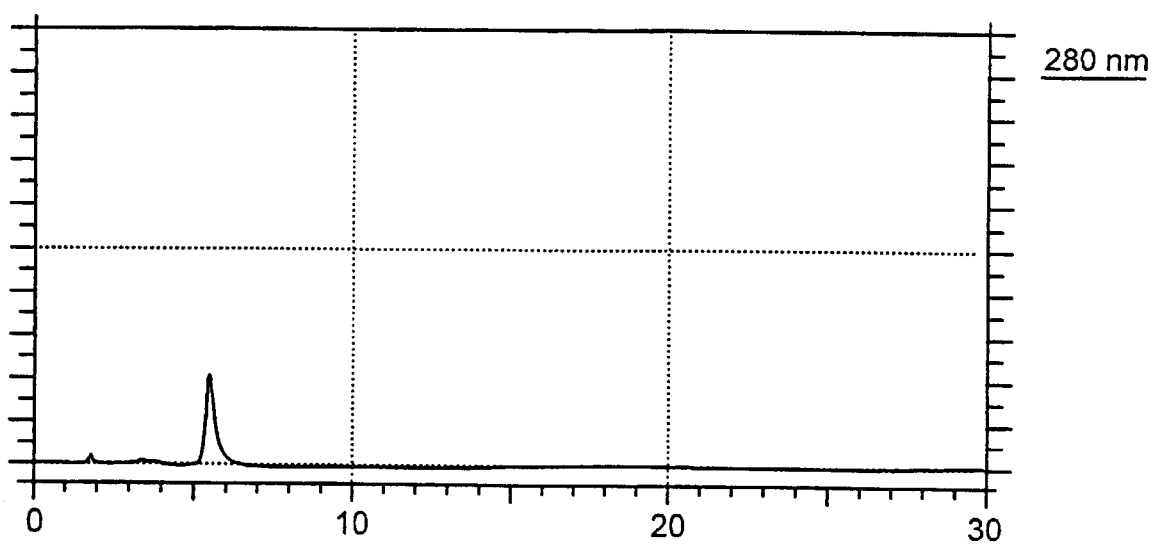
FIG. 6 is a reversed phase HPLC trace of the deprotected linear heptapeptide (7).
Figure 7:
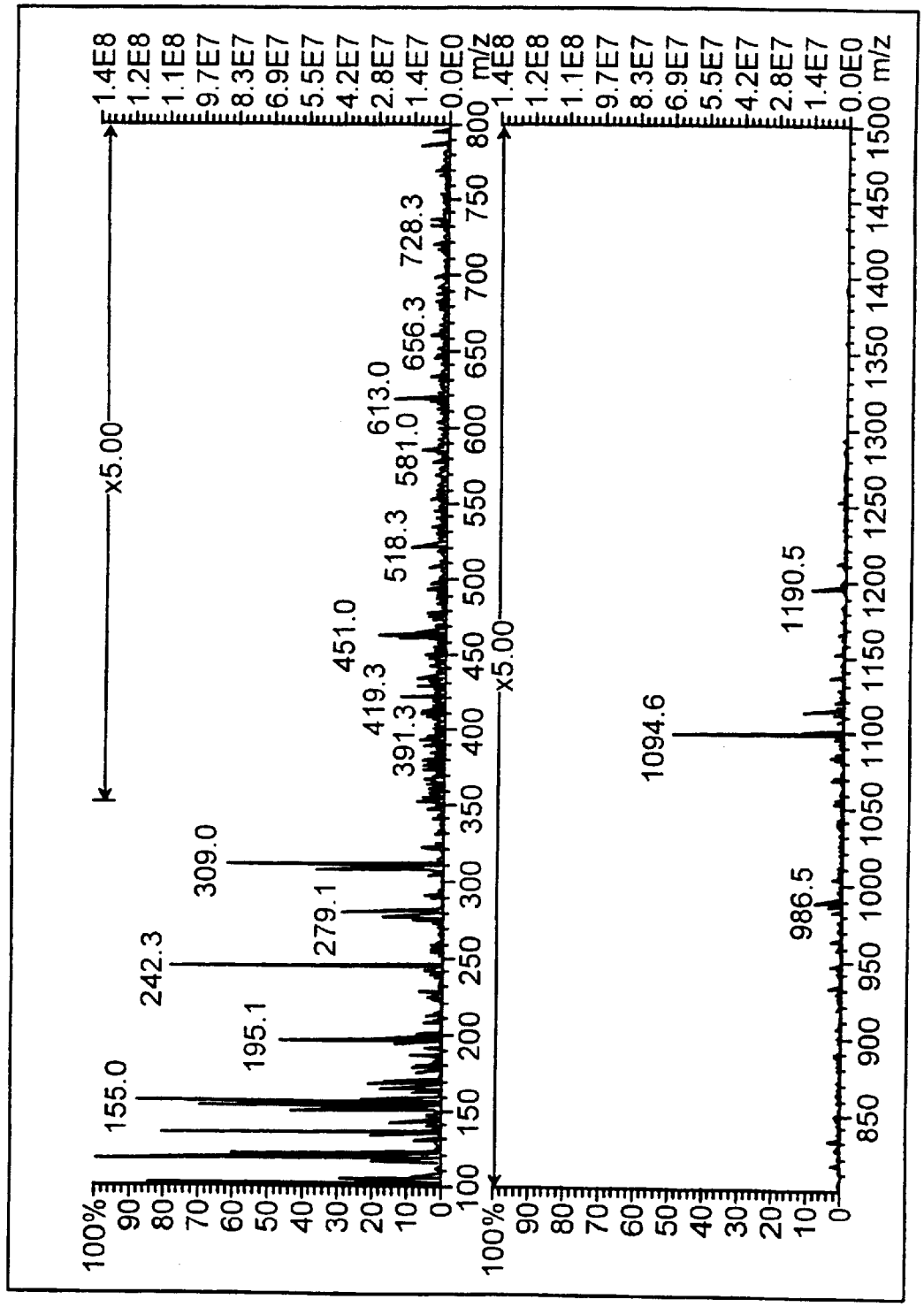
FIG. 7 is a LRFAB mass spectrum of deprotected heptapeptide (7).

1M TBAF (2.1 μL) was added to a solution of the fully protected linear heptapeptide (5.80 mg, 4.50 μmol) in dry THF. After 2 h stirring at 0° C., the mixture was diluted with distilled water and concentrated to a small volume. The remaining solution was diluted with EtOAc and 2N HCl was added to render the aqueous layer acidic. The EtOAc layer was washed three times with water and dried with Na$_2$SO$_4$. Evaporation of the solvent gave the deprotected heptapeptide in quantitative yield (4.3 mg); FABMS 1194.2 (M+H); 1094.2 (M–Boc), see FIG. 5; HRFABMS Calcd for C$_{62}$H$_{100}$N$_7$O$_{14}$Si (M+H) 1194.7098, Found 1194.7089. The deprotected heptapeptide was subjected to a solution of 1M TFA (9.57) μL). After 1 h stirring at room temperature, the solvent was evaporated. Water was added to the residue and the aqueous solution was extracted with EtOAc. The extract was washed with 5% NaHCO$_3$ and water, and dried over Na$_2$SO$_4$. The compound was purified by reversed phase HPLC using a gradient system of CH$_3$CN/H$_2$O see FIG. 6) to give 3.58 mg (91%); FABMS 1094.2 (M+H), see FIG. 7.

AipDidemnin A (8).

Figure 8:
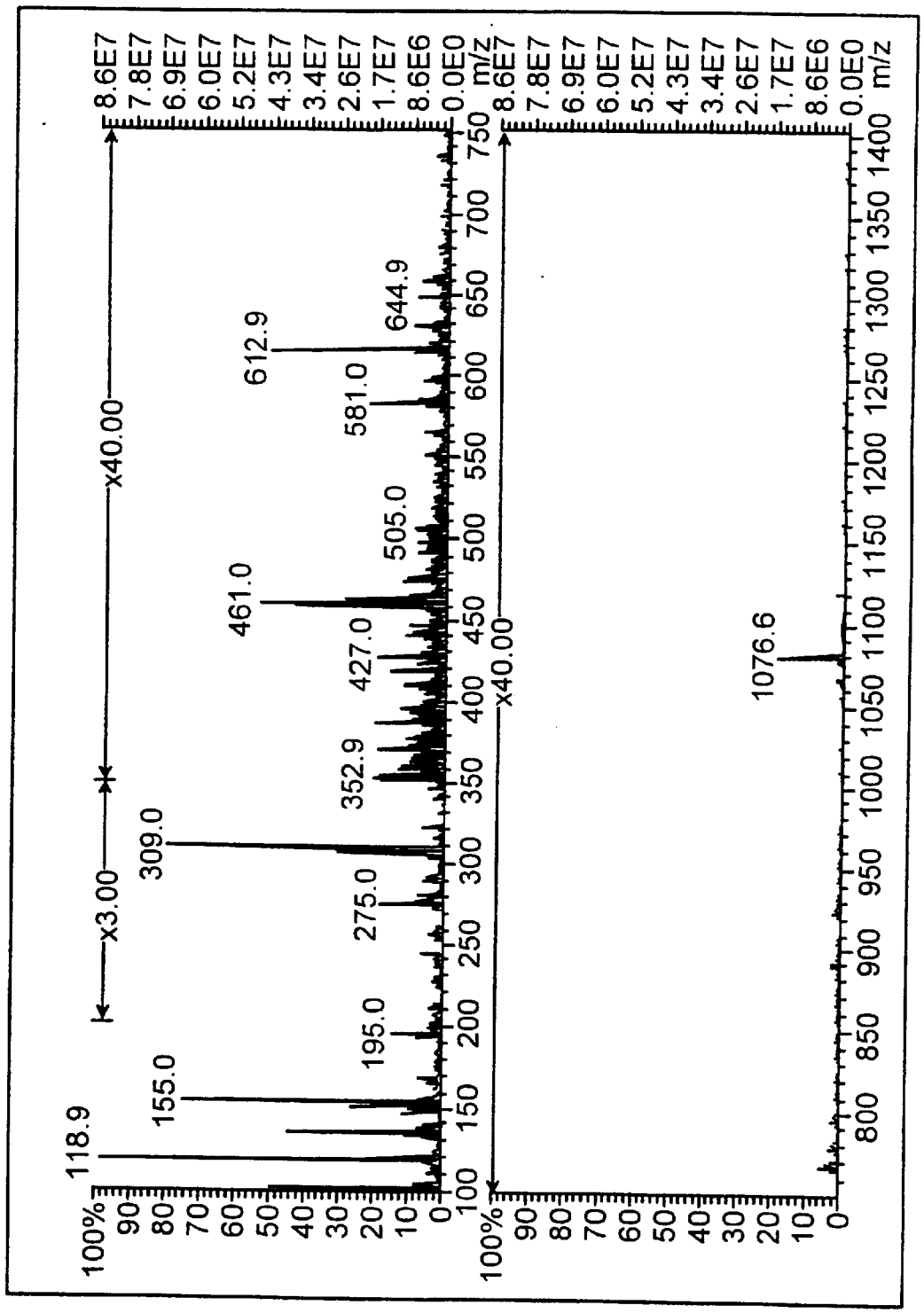
FIG. 8 is a LRFAB mass spectrum of protected amino Hip analog (3).

The linear heptapeptide 7 (3.58 mg, 3.28 μmol) was dissolved in dry THF (0.08 mL), and the solution was cooled to 0° C. EDCI (0.63 mg, 3.28 μmol) in 1.0 mL of THF was added, and the reaction mixture was stirred at 0° C. for 2 h. After storage in the freezer overnight, the solution was diluted with ether. The organic layer was washed with 10% HCl, 5% $NaHCO_3$, and saturated NaCl solutions. The organic layer was dried ($Na_2SO_4$), filtered, and concentrated. The crude oil was purified by reversed phase HPLC using a gradient system of $CH_3CN/H_2O$ to give 1.41 mg (40%) of the protected analogue 3; FABMS 1076.7 (M+H), see FIG. 8; HRFABMS Calcd for $C_{57}H_{86}N_7O_{13}$ (M+H) 1076.6284, Found 1076.6283. The protected compound 3 (1.41 mg) was dissolved in isopropyl alcohol (0.50 mL) and 10% Pd/C catalyst (0.50 mg) was added. The solution was hydrogenated for 3 h. At this time, the catalyst was removed by filtration over celite and the solvent removed to afford the desired compound 8, AipDidemnin A.

TABLE I

Antiviral Activities of Amino Hip Didemnin Analogues[a]

| Compound | ng/mL | HSV/CV-1 Cytotoxicity[b] | Activity[c] |
|---|---|---|---|
| Cbz-[Aip³]-Didemnin A (new compound) | 100 | 10 | + |
| | 50 | 8 | + |
| | 20 | 0 | + |
| | 10 | 0 | − |
| Didemnin A (1) | 100 | 0 | + |
| | 50 | 0 | + |
| | 20 | 0 | + |
| | 10 | 0 | − |

Footnotes: [a]Test performed by Dr. G. R. Wilson in this laboratory; [b]0-least toxic to 16 (toxic); [c]+++ complete inhibition, ++ strong inhibition, + moderate inhibition, − no inhibition.

TABLE II

L1210 Cytotoxicity of Amino Hip Didemnin Analogues[a]

| Compounds | Dose (ng/mL) | | | | $IC_{50}$ (ng/mL) |
|---|---|---|---|---|---|
| | 250 | 25 | 2.5 | 0.25 | |
| | Inhibition (%) | | | | |
| Didemnin A (1) | 100 | 70 | 0 | 0 | 75 |
| Cbz-[Aip³]-Didemnin A (3)[b] | 100 | 87 | 0 | 0 | 85 |
| [Aip³]-Didemnin A (8)[b] | 98 | 20 | 0 | 0 | 100 |

Footnotes: [a]Test performed by Dr. G. R. Wilson in this laboratory; [b]new compounds.

REFERENCES 1. (a) Rinehart, K. L.; Gloer, J. B.; Cook. J. C., Jr.; Mizsak, S. A.; Scahill, T. A.; *J. Am. Chem. Soc.*, 1981, 103, 1857. (b) Rinehart, K. L.; Cook. J. C., Jr.; Pandey, R. C.; Gaudioso, L. A.; Meng, H.,; Moore, M. L.; Gloer, J. B.; Wilson, G. R.; Gutowsky, R. E.; Zierath, P. D.; Shield, L. S.; Li, L. S.; Li, L. H.; Renis, H. E.; McGovern, J. P.; Canonica, P. G. *Pure Appl. Chem.* 1982, 545 2409.
2. Jiang, T. L.; Liu, R. H.; Salmon, S. E. *Cancer Chemother. Pharmacol.* 1983, 11,1.
3. (a) Jones, D. V.; Ajani, J. A.; Blackhorn; R; Daugherty, K.; Levin, B; Pratt, Y. Z.; Abbruzzese, J. L.; *Investigational New Drugs*, 1992, 10, 211. (b) Queisser, W. *Onkologie*, 1992, 15, 454.
4. (a) Rinehart, K. L.; Gloer, J. B.; Hughes, R. G., Jr.; Renis, H. E.; McGovern, J. P.; Synenberg, E. B.; Stringfellow, D. A.; Kuentzel, S. L.; Li, L. H. *Science* (Washington, D.C.) 1981, 212, 933 (b) Canonico, P. G.; Pannier, W. L.; Huggins, J. W.; Rinehart, K. L. *Antimicrob. Agents Chemother.* 1982, 22, 696.
5. Montgomery, D. W.; Zukoski, C. F. *Transplantation*, 1985, 40, 49.
6. Gloer, J. B., Ph. D., Theses, University of Illinois at Urbana-Champaign, 1983.
7. Hossain, M. B., van der Helm, D.; Antel, J.; Sheldrick, G. M.; Sanduja, S. K.; Weinheimer, A. J., *Proc. Natl. Acad. Sci. USA*, 1988, 85, 4118.
8. (a) Banaigs, B.; Jeanty, G.; Francisco, C.; Jouin, P.; Poncet, J.; Heitz, A; Cave, A.; Prome, J. C.; Wahl, M.; Lafargue, F. *Tetrahedron*, 1989, 45, 181; (b) Kessler, H.; Will, M.; Antel, J.; Beck, H.; Sheldrick, G. M.; *Helv. Chim. Acta* 1989, 72, 530. (c) Sakai, R.; Rinehart, K. L.; Kishore, V.; Kundu, B.; Faircloth, G.; Gloer, J. B.; Carney, J. R.; Namikoshi, M.; Sun, F.; Hughes, R. G.; Gravalos, D. C.; Garcia de Quesada, T.; Wilson, G. R.; Heid, R. M. *J. Med. Chem.* 1996, 39, 2819.
9. Shen, G. K.; Zukoski, C. F.; Montgomery, D. W. *Int. J. Immunophrmac*, 1992, 14, 63.
10. Crews, C. M.; Collins, J. L.; Lane, W. S.; Snapper, M. L.; Scheiber, S. L. *J. Biol. Chem.* 1994, 269, 15411.
11. (a) McDermott, J. R.; Benoiton, N. L. *Can. J. Chem.* 1973, 51, 1915, (b) Li, K., Ph.D. Theses, University of Illinois at Urbana-Champaign, 1990.
12. Poduska, J.; Rudinger, N. *Collection Czechoslov. Chem. Commun.* 1959, 24, 3454.
13. Sheehan, J. C.; Hess, G. P. *J. Am. Chem. Soc.* 1955, 77, 1067.
14. (a) Marner, F. J.; Moore, R. E.; Hinotsa, K.; Clardy, J., *J. Org. Chem.* 1977, 42, 2815 (b) Boger, D. L.; Yohannes, D. *J. Org. Chem.* 1988, 53, 487.
15. Carpino, L. A. *J. Am. Chem. Soc.*, 1957, 79, 4427.
16. (a) Bodansky, M. *Principles of Peptide Chemistry*, Speinger-Verlag, New York, 1984, 99. (b) Tarbell, D. S.; Yamamoto, Y.; Pope, B. M. *Proc. Natl. Acad. Sci.* (USA). 1972, 69,730. (c) Itoh, M.; Hagiwara, D.; Kamiya, T. *Bull. Chem. Soc. Jpn.* 1977, 58, 718.
17. Stelakatos, A. Paganou, L.; Zervas, *J. Chem. Soc.* 1966, 1191.
18. Based in part o the following: Schmidt, U.; Kroner, M.; Griesser, H. *Synthesis*, 1989, 832.
19. Kock P.; Nakatani, Y.; Luu, B.; Ourisson, G.; *Bull. Soc. Chim. Jpn.*, 1983, 11, 189.
20. Pearlman, W. M. *Tetrahedron Let*, 1967, 1663.
21. Nagarajan, S. Ph.D.; Theses, University of Illinois at Urbana-Champaign, 1985.
22. Liu, W. L. Chen, S. *Synthesis*, 1980, 223. (b) Corey, E. J.; Suggs, J. W. *Tetrahedron Lett.*, 1975, 31, 2647.
23. Ben-Ishai, D.; Berger, A. *J. Org. Chem.* 1952, 17, 1564.
24. (a) van der Auwera, C.; Anteunis, M. *J. Int. J. Peptide Res.* 1987, 29, 574. (b) Tung, R. D.; Rich, D. H. *J. Am. Chem. Soc.* 1985, 107, 4342.
25. (a) Belleau, B.; Malek, G. *J. Am. Chem. Soc.* 1968, 90, 1651. (b) Bodansky, M. Tolle, J. C.; Gardner, J. D.; Walker, M. D.; Mutt, V. *Int. J. Peptide Protein Res.* 1980, 16, 402.
26. Kopple, K. D.; Nitecki, D. *J. Am. Chem. Soc.* 1962, 84, 4457.
27. Witten, J. L.; Schauffer, M. H.; O'Shea, M.; Cook, J. C.; Hemling, M. E.; Rinehart, K. L. *Biochem Biophys. Res. Commun.* 1984, 124, 350.
28. Rinehart, K. L.; Sakai, R.; Kishore, V.; Sullins; D. W.; Li,. *J. Org. Chem.* 1992, 57, 3007.

29. (a) Strube, R. E. *Org. Cynth. Coll. Vol.* 1963, 4, 417. (b) Maibaum, J.; Rich, D. H., *J. Org. Chem.*, 1988, 53, 869. (c) Paul, R.; Anderson, G. W. *J. Am. Chem. Soc.*, 1960, 82, 4597.

30. Hamada, Y.; Kondo, Y.; Shibata, M.; Shiori, T. *J. Am. Chem. Soc.*, 1989, 111, 669.

What is claimed is:

1. The compound Cbz-[Aip³]-Didemnin A.

2. The compound [Aip³]-Didemnin A.

3. A synthetic process for the formation of an Amino Hip analogue of Didemnin A, said process comprising the steps of:

(a) forming a linear heptapeptide by coupling two subunits, Cbz-D-MeLeuThr(Ome₂TyrBoc)OH (5) and H-IstAipLeuProOTMSe (6):

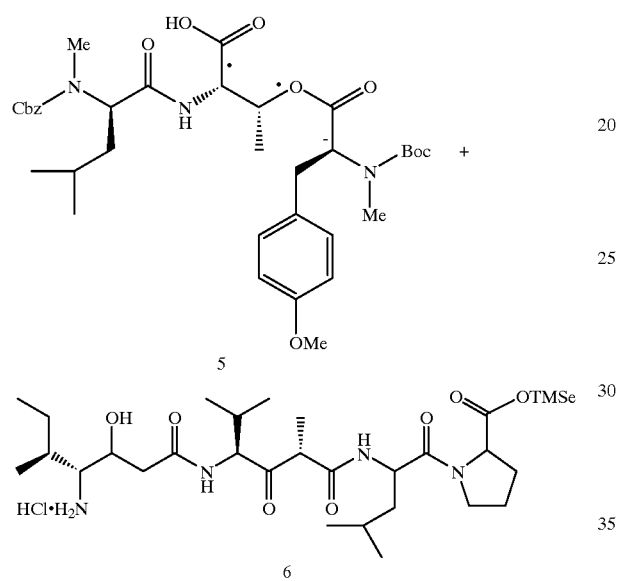

5

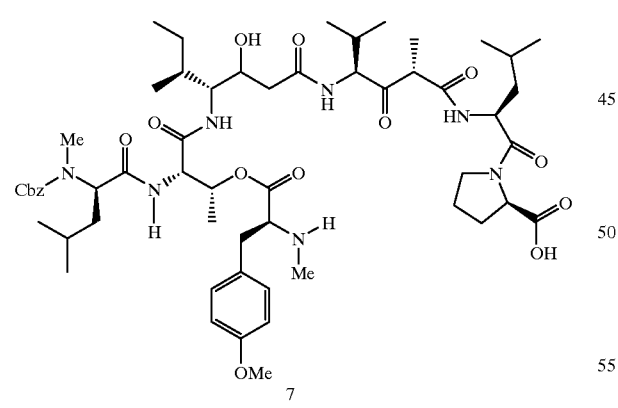

6 followed by deprotection to yield a linear heptapeptide (7); and

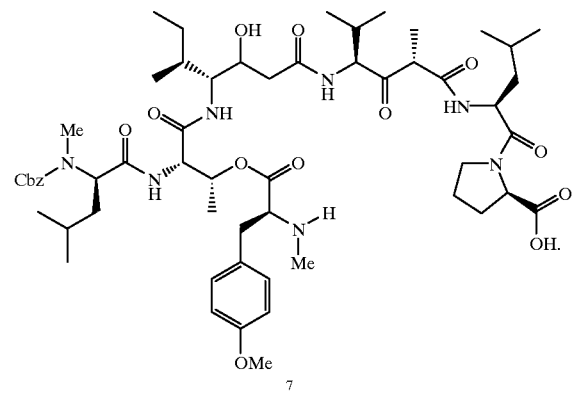

7

(b) cyclizing the heptapeptide (7) to obtain the amino Hip (Aip) analog of Didemnin A.

4. An intermediate compound having the formula 5:

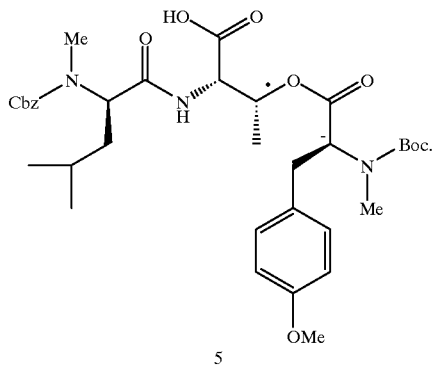

5

5. An intermediate compound having the formula 6:

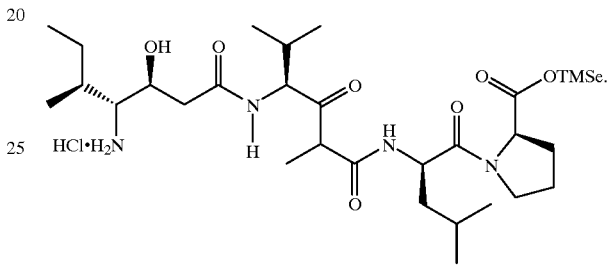

6

6. An intermediate compound having the formula 7:

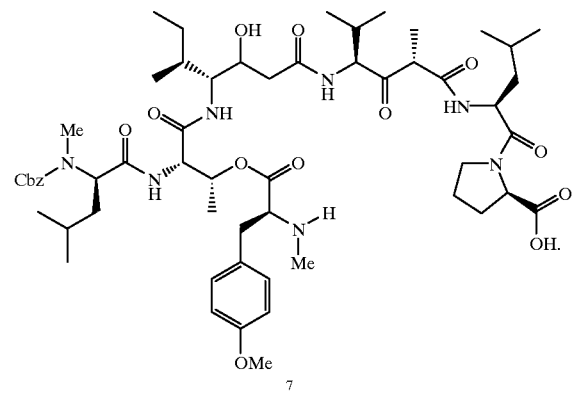

7

7. A pharmaceutical composition comprising Cbz-[Aip³] didemnin A, and an optional pharmaceutically acceptable excipient, diluent or carrier.

8. A pharmaceutical composition comprising [Aip³] didemnin A and an optional pharmaceutically acceptable excipient, diluent or carrier.

* * * * *